United States Patent
Burns et al.

(10) Patent No.: US 7,122,550 B2
(45) Date of Patent: Oct. 17, 2006

(54) PROTEIN KINASE INHIBITORS

(75) Inventors: Christopher John Burns, Seddon (AU); Xianyong Bu, Rosanna East (AU); Andrew Frederick Wilks, South Yarra (AU)

(73) Assignee: Cytopia Pty Ltd, Melbourne (AU)

( * ) Notice: Subject to any disclaimer, the term of this patent is extended or adjusted under 35 U.S.C. 154(b) by 102 days.

(21) Appl. No.: 10/469,303

(22) PCT Filed: May 23, 2003

(86) PCT No.: PCT/AU03/00629

§ 371 (c)(1),
(2), (4) Date: Aug. 29, 2003

(87) PCT Pub. No.: WO03/099796

PCT Pub. Date: Dec. 4, 2003

(65) Prior Publication Data

US 2004/0235862 A1 Nov. 25, 2004

Related U.S. Application Data

(60) Provisional application No. 60/399,070, filed on Jul. 26, 2002.

(30) Foreign Application Priority Data

May 23, 2002 (AU) .................... PS2515

(51) Int. Cl.
*A61K 31/4965* (2006.01)
*C07D 241/00* (2006.01)
*C07D 241/02* (2006.01)
*C07D 401/00* (2006.01)

(52) U.S. Cl. ................... 514/255.05; 514/255.06; 544/336; 544/405

(58) Field of Classification Search .................. None
See application file for complete search history.

(56) References Cited

FOREIGN PATENT DOCUMENTS

WO   WO 02/060492    8/2002

OTHER PUBLICATIONS

Duhé et al, "Negative Regulation of Janus Kinases" Cell Biochemistry and Biophysics, vol. 34(1), pp. 17-59 (2001).*
Scapin, G. "Structural biology in drug design: selective protein kinase inhibitors" Drug Discovery Today, vol. 7(11), pp. 601-611 (Jun. 2002).*
Ding et al., J. Am. Chem. Soc. (2002) 124(8):1594-1596.
International Search Report mailed on Jul. 4, 2003, for PCT patent application No. PCT/AU03/00629 filed on May 23, 2003, 3 pages.
Miyaura and Suzuki, Chem Rev. (1995) 95:2457.
Spiotto and Chung, Prostate (2000) 42:88-98.
Stille, Angew. Chem., Int. Ed. Engl., (1986) 25:508.

* cited by examiner

*Primary Examiner*—James O. Wilson
*Assistant Examiner*—Zachary C. Tucker
(74) *Attorney, Agent, or Firm*—Morrison & Foerster LLP

(57) ABSTRACT

A compound of the general formula:

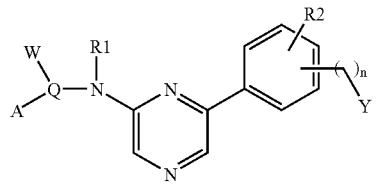

or pharmaceutically acceptable salts, hydrates, solvates, crystal forms of diastereomers thereof is described. A method of treating protein kinase-associated disease states using the compound of Formula I is also described.

11 Claims, 3 Drawing Sheets

Dose-response curves for R and S enantiomers of representative 2-(α-methyl benzylamino)-pyrazine possessing inhibitory activity in Tel-Jak2 transformed cell line Figure 1: Dose-response curves for R and S enantiomers of representative 2-(α-methyl benzylamino)-pyrazine possessing inhibitory activity in Tel-Jak2 transformed cell line
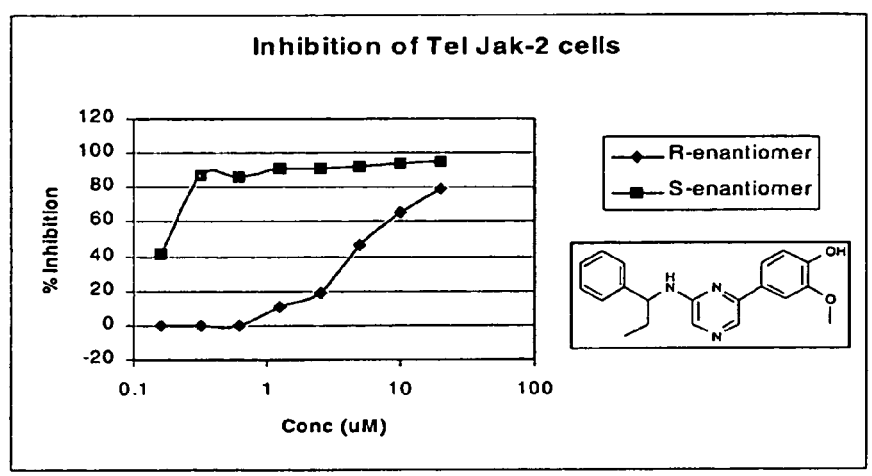

Figure 2: Kinase Inhibition Activity Of Representative 2-(α-methyl benzylamino)-pyrazines. Kinase assays were performed as described in the methods section. Figure 2A, CYC10124 (exemplified as Chemistry 141 in table 1) exhibits potent inhibitory activity against the c-KIT, TIE2 and ABL protein kinases. Figure 2B, CYC10268 (exemplified as Chemistry 268 in table 1) exhibits potent inhibitory activity against c-FMS. Figure 2C, CYC10119 (exemplified as Chemistry 136 in table 1) exhibits potent inhibitory activity against JAK2 and c-KIT.

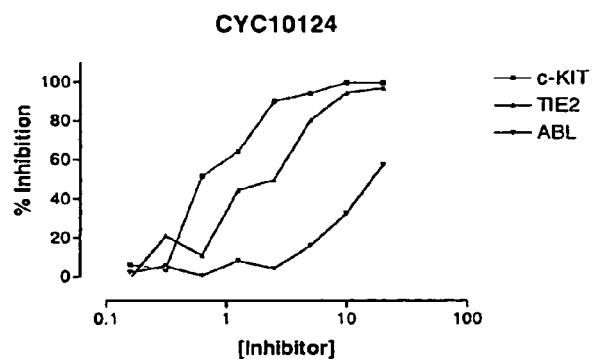

Figure 2A

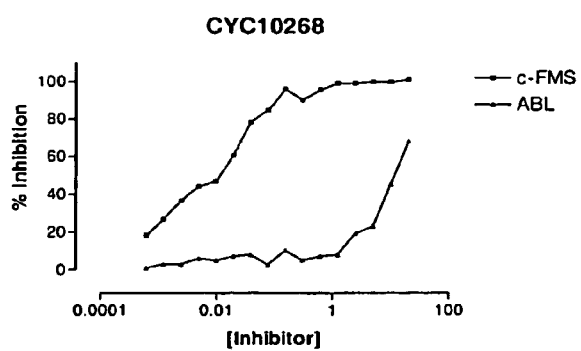

Figure 2B

PROTEIN KINASE INHIBITORS

CROSS-REFERENCE TO RELATED APPLICATION

This application is the national phase of PCT application PCT/AU03/00629 having an international filing date of 23 May 2003, and claims priority from U.S. application No. 60/399,070 filed 26 Jul. 2002 and Australian application no. PS2515 filed 23 May 2002. The contents of these documents are incorporated herein by reference.

FIELD OF THE INVENTION

The present invention relates to the field of inhibitors of protein kinases.

BACKGROUND OF THE INVENTION

Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Protein kinases include members of the Protein Tyrosine Kinase family (PTKs), which in turn can be divided into the cytoplasmic PTKs (CTKs) and the receptor PTKs (RTKs). The cytoplasmic PTKs include the SRC family, (including: BLK; FGR; FYN; HCK; LCK; LYN; SRC;YES and YRK); the BRK Family (including: BRK; FRK, SAD; and SRM); the CSK family (including: CSK and CTK); the BTK family, (including BTK; ITK; TEC; MKK2 and TXK), the Janus kinase family, (including: JAKI, JAK2, JAK3 and Tyk2), the FAK family (including, FAK and PYK2); the Fes family (including FES and FER), the ZAP70 family (including ZAP70 and SYK); the ACK family (including ACK1 and ACK2); and the Ab1 family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRα, PDGFRβ, CSF1R, KIT, FLK2); the VEGF-Receptor family (including; FLT1, FLK1 and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family including LMR1, LMR2 and LMR3; and the SuRTK106 family (including SuRTK106).

Similarly, the serine/threonine specific kinases comprise a number of distinct sub-families, including; the extracellular signal regulated kinases, (p42/ERK2 and p44/ERKI); c-Jun NH2-terminal kinase (JNK); cAMP-responsive element-binding protein kinases (CREBK); the cyclin dependent kinases (CDKs); cAMP-dependent kinase (CAPK); mitogen-activated protein kinase-activated protein kinase (MAPK and its relatives); stress-activated protein kinase p38/SAPK2; mitogen-and stress-activated kinase (MSK); protein kinases, PKA, PKB and PKC inter alia.

Additionally, the genomes of a number of pathogenic organisms possess genes encoding protein kinases. For example, the malarial parasite *Plasmodium falciparum* and viruses such as HPV and Hepatitis viruses appear to bear kinase related genes.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect. Diseases where aberrant kinase activity has been implicated include: diabetes; restenosis; atherosclerosis; fibrosis of the liver and kidney; ocular diseases; myelo- and lymphoproliferative disorders; cancer such as prostate cancer, colon cancer, breast cancer, head and neck cancer, leukemia and lymphoma; and, auto-immune diseases such as Atopic Dermatitis, Asthma, rheumatoid arthritis, Crohn's disease, psoriasis, Crouzon syndrome, achondroplasia, and thanatophoric dysplasia.

SUMMARY OF THE INVENTION

The present inventors have found that a group of compounds based upon a disubstituted pyrazine scaffold are inhibitors of protein kinases.

This invention is therefore directed to compounds that potentially modulate Protein Kinase signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of tumor.

Accordingly, in a first aspect the present invention consists in a compound of the general formula

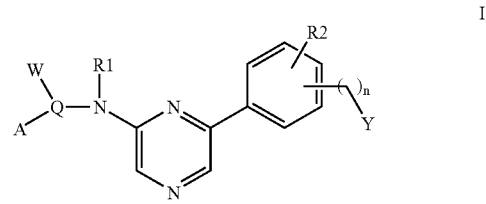

or pharmaceutically acceptable salts, hydrates, solvates, crystal forms or diastereomers thereof, wherein:

R1 is H, $C_{1-4}$ alkyl

Q is a bond, or $C_{1-4}$ alkyl

A is aryl, hetaryl optionally substituted with 0–3 substituents independently chosen from halogen, $C_{1-4}$ alkyl, $CH_2F$, $CHF_2$, $CF_3$, CN, aryl, hetaryl, $OCF_3$, $OC_{1-4}$ alkyl, $OC_{2-5}$alkylNR4R5, Oaryl, Ohetaryl, $CO_2R4$, CONR4R5, nitro, NR4R5, $C_{1-4}$ alkylNR4R5, NR6 $C_{1-4}$alkylNR4R5, NR4COR5, NR6CONR4R5, $NR4SO_2R5$; and R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3–8 membered ring optionally containing an atom selected from O, S, NR7; and R6 is selected from H, $C_{1-4}$ alkyl; and R7 is selected from H, $C_{1-4}$ alkyl, aryl, hetaryl, $C_{1-4}$ alkyl aryl, $C_{1-4}$ alkyl hetaryl.

R2 is 0–2 substituents independently selected from halogen, $C_{1-4}$alkyl, OH, $OC_{1-4}$ alkyl, $CH_2F$, $CHF_2$, $CF_3$, $OCF_3$, CN, $C_{1-4}$alkylNR8R9, $OC_{1-4}$alkylNR8R9, $CO_2R8$, CONR8R9, NR8R9, NR8COR9, NR10CONR8R9, $NR8SO_2R9$; and R8, R9 are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3–8 membered ring optionally containing an atom selected from O, S, NR11; and R10 is selected from H, $C_{1-4}$ alkyl, aryl or hetaryl; and R11 is selected from H, $C_{1-4}$ alkyl, aryl, hetaryl, $C_{1-4}$ alkyl aryl, $C_{1-4}$ alkyl hetaryl.

Y is halogen, OH, NR12R13, NR12COR13, NR12CONR13, $N12SO_2R13$; and R12, and R13 are each independently H, $CH_2F$, $CHF_2$, $CF_3$, CN, $C_{1-4}$ alkyl, $C_{1-4}$ alkyl cycloalkyl, $C_{1-4}$ alkyl cyclohetalkyl, or may be joined to form an optionally substituted 3–6 membered ring optionally containing an atom selected from O, S, NR14 and R14 is selected from H, $C_{1-4}$ alkyl.

n=0–4

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3–8 membered ring optionally containing an atom selected from O, S, NR17 and R17 is selected from H, $C_{1-4}$ alkyl;

wherein when Y is OH or $NHCOCH_3$ then R2 is 1–2 substituents and wherein when Y is $NH_2$ and R2 is absent then Y is in the para position.

In a second aspect the present invention consists in a composition comprising a carrier and at least one compound of the first aspect of the invention.

In a third aspect the present invention consists in a method of treating a protein kinase-associated disease state, the method comprising administering a therapeutically effective amount of at least one compound of the first aspect of the invention or a therapeutically effective amount of a composition of the second aspect of the invention.

BRIEF DESCRIPTION OF THE FIGURES

FIG. 1 describes dose-response curves for R and S enantiomers of representative 2-(α-methyl benzylamino)-pyrazine.

FIG. 2 describes the kinase inhibition activity of representative 2-(α-methyl benzylamino)-pyrazines. FIGS. 2A, 2B and 2C describe the inhibitory activity of CYC10124, CYC10268 and CYC10119 respectively.

DETAILED DESCRIPTION

Figure 2C:
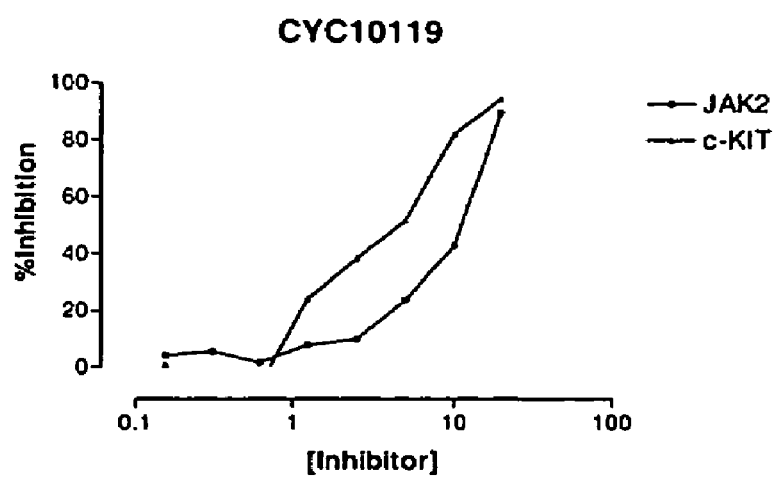

This invention is directed to compounds that potentially modulate Protein Kinase signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of tumor.

Accordingly, in a first aspect the present invention consists in a compound of the general formula

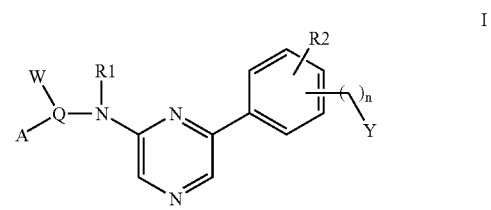

or pharmaceutically acceptable salts, hydrates, solvates, crystal forms or diastereomers thereof, wherein:

R1 is H, $C_{1-4}$ alkyl

Q is a bond, or $C_{1-4}$ alkyl

A is aryl, hetaryl optionally substituted with 0–3 substituents independently chosen from halogen, $C_{1-4}$ alkyl, $CH_2F$, $CHF_2$, $CF_3$, CN, aryl, hetaryl, $OCF_3$, $OC_{1-4}$ alkyl, $OC_{2-5}$alkylNR4R5, Oaryl, Ohetaryl, $CO_2R4$, CONR4R5, nitro, NR4R5, $C_{1-4}$ alkylNR4R5, NR6 $C_{1-4}$alkylNR4R5, NR4COR5, NR6CONR4R5, $NR4SO_2R5$; and R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3–8 membered ring optionally containing an atom selected from O, S, NR7; and R6 is selected from H, $C_{1-4}$ alkyl; and R7 is selected from H, $C_{1-4}$ alkyl, aryl, hetaryl, $C_{1-4}$ alkyl aryl, $C_{1-4}$ alkyl hetaryl.

R2 is 0–2 substituents independently selected from halogen, $C_{1-4}$alkyl, OH, $OC_{1-4}$alkyl, $CH_2F$, $CHF_2$, $CF_3$, $OCF_3$, CN, $C_{1-4}$alkylNR8R9, $OC_{1-4}$alkylNR8R9, $CO_2R8$, CONR8R9, NR8R9, NR8COR9, NR10CONR8R9, $NR8SO_2R9$; and R8, R9 are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3–8 membered ring optionally containing an atom selected from O, S, NR11; and R10 is selected from H, $C_{1-4}$ alkyl, aryl or hetaryl; and R11 is selected from H, $C_{1-4}$ alkyl, aryl, hetaryl, $C_{1-4}$ alkyl aryl, $C_{1-4}$ alkyl hetaryl.

Y is halogen, OH, NR12R13, NR12COR13, NR12CONR13, $N12SO_2R13$; and R12, and R13 are each independently H, $CH_2F$, $CHF_2$, $CF_3$, CN, $C_{1-4}$ alkyl, $C_{1-4}$ alkyl cycloalkyl, $C_{1-4}$ alkyl cyclohetalkyl, or may be joined to form an optionally substituted 3–6 membered ring optionally containing an atom selected from O, S, NR14 and R14 is selected from H, $C_{1-4}$ alkyl.

n=0–4

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3–8 membered ring optionally containing an atom selected from O, S, NR17 and R17 is selected from H, $C_{1-4}$ alkyl;

wherein when Y is OH or NHCOCH$_3$ then R2 is 1–2 substituents and wherein when Y is NH$_2$ and R2 is absent then Y is in the para position.

In the above description it will be appreciated that:

$C_{1-4}$ alkyl means a straight or branched alkyl chain

Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3–8 membered saturated ring

Cyclohetalkyl means a 3–8 membered saturated ring containing 1–3 heteroatoms selected from O, S, NR18, where R18 is H, $C_{1-4}$ alkyl, aryl, hetaryl.

In a further preferred embodiment the compound is selected from compounds of the general formula II.

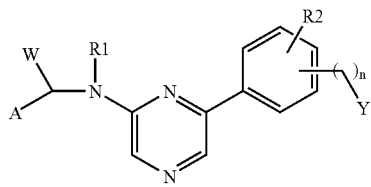

II or pharmaceutically acceptable salts, hydrates, solvates, crystal forms or diastereomers thereof, wherein:

R1 is H, $C_{1-4}$ alkyl

Q is a bond, or $C_{1-4}$ alkyl

A is aryl, hetaryl optionally substituted with 0–3 substituents independently chosen from halogen, $C_{1-4}$ alkyl, CH$_2$F, CHF$_2$, CF$_3$, CN, aryl, hetaryl, OCF$_3$, OC$_{1-4}$ alkyl, OC$_{2-5}$alkylNR4R5, Oaryl, Ohetaryl, CO$_2$R4, CONR4R5, NR4R5, $C_{1-4}$ alkylNR4R5, NR6 $C_{1-4}$alkylNR4R5, NR4COR5, NR6CONR4R5, NR4SO$_2$R5; and R4, R5 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3–8 membered ring optionally containing an atom selected from O, S, NR7; and R6 is selected from H, $C_{1-4}$ alkyl; and R7 is selected from H, $C_{1-4}$ alkyl, aryl, hetaryl, $C_{1-4}$ alkyl aryl, $C_{1-4}$ alkyl hetaryl.

R2 is 0–2 substituents independently selected from halogen, $C_{1-4}$alkyl, OH, OC$_{1-4}$alkyl, CH$_2$F, CHF$_2$, CF$_3$, OCF$_3$, CN, $C_{1-4}$alkylNR8R9, OC$_{1-4}$alkylNR8R9, CO$_2$R8, CONR8R9, NR8R9, NR8COR9, NR10CONR8R9, NR8SO$_2$R9; and R8, R9 are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3–8 membered ring optionally containing an atom selected from O, S, NR11; and R10 is selected from H, $C_{1-4}$ alkyl, aryl or hetaryl; and R11 is selected from H, $C_{1-4}$ alkyl, aryl, hetaryl, $C_{1-4}$ alkyl aryl, $C_{1-4}$ alkyl hetaryl.

Y is halogen, OH, NR12R13, NR12COR13, NR12CONR13, N12SO$_2$R13; and

R12, and R13 are each independently H, CH$_2$F, CHF$_2$, CF$_3$, CN, $C_{1-4}$ alkyl, $C_{1-4}$ alkyl cycloalkyl, $C_{1-4}$ alkyl cyclohetalkyl, or may be joined to form an optionally substituted 3–6 membered ring optionally containing an atom selected from O, S, NR14 and R14 is selected from H, $C_{1-4}$ alkyl.

n=0–4

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, OC$_{1-4}$alkyl, NR15R16; and R15, and R16 are each independently H, $C_{1-4}$ alkyl, $C_{1-4}$ alkyl cycloalkyl, $C_{1-4}$ alkyl cyclohetalkyl, or may be joined to form an optionally substituted 3–8 membered ring optionally containing an atom selected from O, S, NR17 and R17 is selected from H, $C_{1-4}$ alkyl;

wherein when Y is OH or NHCOCH$_3$ then R2 is 1–2 substituents and wherein when Y is NH$_2$ and R2 is absent then Y is in the para position.

In the above description it will be appreciated that:

$C_{1-4}$ alkyl means a straight or branched alkyl chain

Aryl means unsubstituted or optionally substituted phenyl or naphthyl.

Hetaryl means an unsubstituted or optionally substituted 5- or 6-membered heteroaromatic ring containing one or more heteroatoms selected from O, N, S.

Cycloalkyl means a 3–8 membered saturated ring

Cyclohetalkyl means a 3–8 membered saturated ring containing 1–3 heteroatoms selected from O, S, NR18, where R18 is H, $C_{1-4}$ alkyl, aryl, hetaryl.

The compounds of this invention include all conformational isomers (eg. cis and trans isomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases, such as JAK comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

In a still further preferred embodiment the compound possesses S chirality at the chiral carbon bearing W, where W is $C_{1-4}$ alkyl. The compound can be used as a purified isomer or as a mixture of any ratio of isomers. It is however preferred that the mixture comprises at least 70%, 80%, 90%, 95%, or 99% of the preferred isomer.

In a still further preferred embodiment the compound is selected from the compounds set out in Table 1.

In a second aspect the present invention consists in a composition comprising a carrier and at least one compound of the first aspect of the invention.

In a third aspect the present invention consists in a method of treating a protein kinase-associated disease state, the method comprising administering a therapeutically effective amount of at least one compound of the first aspect of the invention or a therapeutically effective amount of a composition of the second aspect of the invention.

In a preferred embodiment, the disease state involves a receptor tyrosine kinase selected from the group consisting of EGF, HER2, HER3, HER4, IR, IGF-1R, IRR, PDGFR.alpha., PDGFR.beta., CSFIR, C-Kit, C-fms,Flk-1R, Flk4, KDR/Flk-1, Flt-1, FGFR-1R, FGFR-2R, FGFR-3R and FGFR-4R.

In another preferred embodiment, the disease state involves a cellular tyrosine kinase selected from the group consisting of Src, Frk, Btk, Csk, Ab1, ZAP70, Fes/Fps, Fak, Ack, Yes, Fyn, Lyn, Lck, Blk, Hck, Fgr and Yrk.

In a further preferred embodiment, the disease state involves a tyrosine kinase selected from the group consisting of JAK1, JAK2, JAK3 and TYK2.

In a yet further preferred embodiment, the disease state involves a serine/threonine kinase selected from the group consisting of ERK2, c-Jun, p38 MAPK, PKA, PKB, PKC, a cyclin-dependent kinase, CDK1, CDK2, CDK3, CDK4, CDK5, CDK6, CDK7, CDK8, CDK9, CDK10, and CDK11.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV), Cancer, such as Leukemia, Lymphoma and Prostate Cancer.

In one embodiment, the method of the invention is used in the treatment of sarcomas, carcinomas and/or leukemias. Exemplary disorders for which the subject method can be used alone or as part of a treatment regimen include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the method of the invention is be used to treat disorders such as carcinomas forming from tissue of the breast, prostate, kidney, bladder or colon.

In other embodiments, the method of the invention is used to treat hyperplastic or neoplastic disorders arising in adipose tissue, such as adipose cell tumors, e.g., lipomas, fibrolipomas, lipoblastomas, lipomatosis, hibemomas, hemangiomas and/or liposarcomas.

As used herein the term "protein kinase-associated disease state" refers to those disorders which result from aberrant protein kinase activity, in particular JAK activity and/or which are alleviated by inhibition of one or more of these enzymes.

In further aspects the present invention provides the use of the compounds described in the preparation of medicaments for the treatment of protein kinase-associated disease states including JAK-associated disease states.

As used herein the term "JAK", "JAK kinase" or "JAK family" refers to protein tyrosine kinases which possess the characterizing features of JAK1, JAK2, JAK3 and TYK as described herein.

The present invention provides pharmaceutical compositions comprising at least one of the compounds of the formula I or II capable of treating a protein kinase-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I or II may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which JAK inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following:

cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen and cyclooxygenase inhibitors such as rofecoxib, steroids such as prednisolone or dexamethasone, gold compounds, antiproliferative agents such as methotrexate, FK506 (tacrolimus, Prograf), mycophenolate mofetil, cytotoxic drugs such as azathioprine, VP-16, etoposide, fludarabine, cisplatin and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of, the present invention they may be used for example in amounts as noted in the Physician Desk Reference (PDR) or as otherwise determined by one of ordinary skill in the art.

In the treatment or prevention of conditions which require protein kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more clearly understood preferred forms thereof will now be described by reference to the following non-limiting Examples.

MATERIALS AND METHODS

Compound Synthesis

Compounds are generally prepared in a 2-step process starting from 2,6-dichloropyrazine.

The first step is a nucleophilic aromatic substitution to generate a monoamino-monohalo intermediate. (Scheme 1).

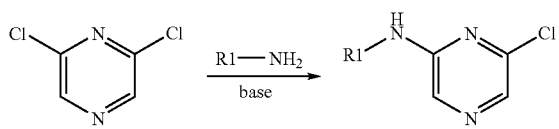

Scheme 1

The nucleophilic aromatic substitution is typically carried out by addition of a primary amine to the di-halogenated heterocycle in a solvent such as ethanol, isopropanol, tert-butanol, dioxane, THF, DMF, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include Pd(OAc)$_2$/P(t-Bu)$_3$, Pd$_2$(dba)$_3$/BINAP and Pd(OAc)$_2$/BINAP. These reactions are typically out in solvents such as toluene or dioxane, in the presence of bases such as caesium carbonate or sodium or potassium tert-butoxide at temperatures ranging from room temperature to reflux.

The amines employed in the first step of the synthesis of these compounds are obtained commercially or are prepared using methods well known to those skilled in the art. Of particular interest are α-methylbenzylamines which may be prepared through reduction of oximes (Scheme 2). Typical reductants include lithium aluminium hydride, hydrogen gas in the presence of palladium on charcoal catalyst, Zn in the presence of hydrochloric acid, sodium borohydride in the presence of a Lewis acid such as TiCl$_3$, ZrCl$_4$, NiCl$_2$ and MoO$_3$, or sodium borohydride in conjunction with Amberlyst H15 ion exchange resin and LiCl.

Scheme 2

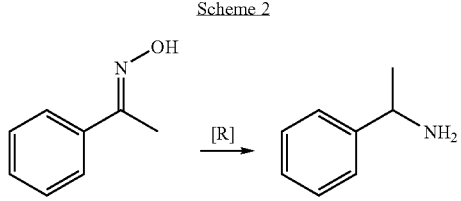

α-Methyl benzylamines of high optical purity may be prepared from chiral α-methyl benzyl alcohols using methods well known to those skilled in the art. Such methods include derivatisation of the hydroxyl as a mesylate or tosylate and displacement with a nitrogen nucleophile, such as phthalimide or azide which is then converted to the primary amine using conventional synthetic methods; or, displacement of the hydroxyl with a suitable nitrogen nucleophile under Mitsunobu conditions. The chiral α-methyl benzyl alcohols may be obtained through chiral reduction of the corresponding ketones. Chiral reducing methods are now well known in organic chemistry and include enzymatic processes, asymmetric hydrogenation procedures and chiral oxazaborolidines.

The second step of the synthesis typically involves a palladium mediated cross-coupling of the monoamino-monochloro intermediate with a suitably functionalised coupling partner. Typical coupling partners are boronic acids (Suzuki coupling: see for example Miyaura, N. and Suzuki, Chem Rev. 1995, 952457) or stannanes (Stille coupling: see for example Stille, J. K., Angew. Chem., Int. Ed. Engl., 1986, 25, 508) (Scheme 3).

Scheme 3

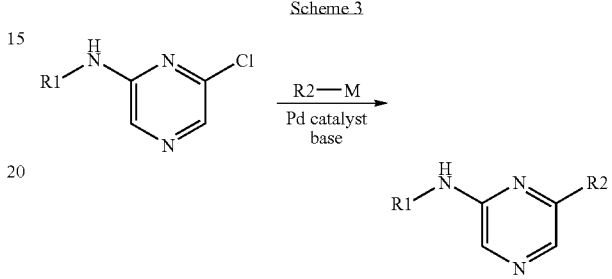

The Suzuki coupling is the preferred coupling method and is typically performed in a solvent such as DME, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from [Pd(PPh$_3$)$_4$], Pd(OAc)$_2$, [PdCl$_2$(dppf)], Pd$_2$(dba)$_3$/P(t-Bu)$_3$.

The products formed from this reaction sequence may be further derivatised using techniques well-known to those skilled in the art. Alternatively, derivatisation of the mono-amino mono-chloropyrazine may be undertaken prior to displacement of the 6-chloro substituent. This derivatisation typically involves functionality originally present on the amine species and employs methods well known to those skilled in the art.

Representative syntheses are reported below.

EXAMPLE 1

6-Chloro-N-[(1R)-1-phenylethyl]pyrazin-2-amine

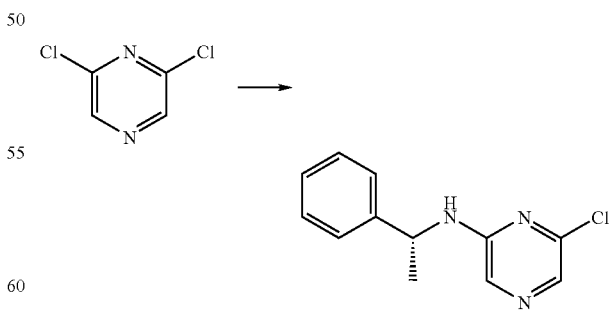

A solution of R-α-methylbenzylamine (0.57 g, 4.7 mmol) and 2,6-dichloropyrazine (0.6388 g, 4.29 mmol) in dioxane (2.5 mL) was heated at reflux under N$_2$ for 48 hours. The solvent was removed and the product crystallised from toluene-hexane (0.82 g, 82%).

¹H-n.m.r. (CDCl₃) δ 1.58 (d, J=6.6 Hz, 3H, CH₃), 4.88 (m, 1H, CH), 5.07 (d, 1H, NH), 7.24–7.36 (m, 5H, Ar—H), 7.61 (s, 1H, pyraz-H), 7.79 (s, 1H, pyraz-H).

EXAMPLE 2

2-Methoxy-4-(6-{[(1R)-1-phenylethyl]amino}pyrazin-2-yl)phenol

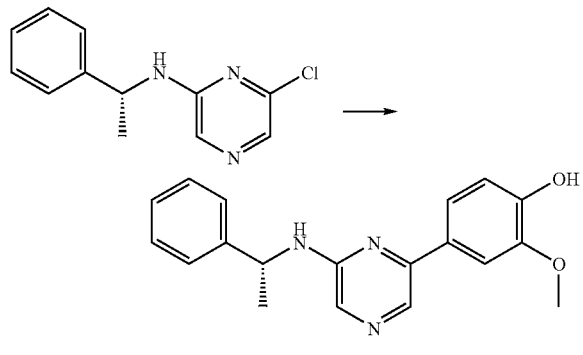

Under a nitrogen atmosphere a mixture of 6-chloro-N-[(1R)-1-phenylethyl]pyrazin-2-amine (0.611 g, 2.61 mmol), 4-(4,4,5,5-tetramethyl-1,3,2-dioxaborolan-2-yl)phenol (0.785 g, 3.14 mmol), tetrakis(triphenylphosphine)palladium(0) (0.30 g, 0.26 mmol) and toluene (3 mL) was treated with 2M aqueous sodium carbonate solution (1.6 mL, 2.6 mmol). The resulting mixture was stirred vigorously whilst being heated under reflux for 24 hours. Once cool ethyl acetate was added and the mixture dried (MgSO₄) and filtered. Removal of solvent in vacuo then yielded crude product, which was purified by column chromatography using dichloromethane:diethyl ether (99:1→90:10) as eluent: (0.619 g, 74%).

¹H-n.m.r. (CDCl₃) δ 1.72 (d, 3H, J=6.9 Hz, CH₃), 4.06 (s, 3H, OCH₃), 4.90 (m, 1H, CH), 5.75 (br s, 1H, NH), 6.98 (d, 1H, J=8.1 Hz, ArH), 7.26–7.46 (m, 7H, Ar—H), 7.97 (s, 1H, pyraz-H), 8.20 (s, 1H, pyraz-H).

EXAMPLE 3

6-Chloro-N-[(1R)-1-(3-methoxyphenyl)ethyl]pyrazin-2-amine

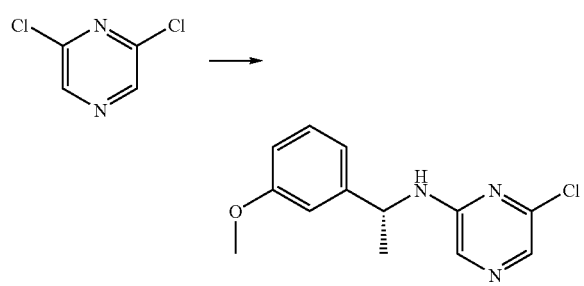

In a procedure analogous to Example 1, reaction of R-α-methylbenzylamine (1.0 g, 6.6 mmol) and 2,6-dichloropyrazine (0.440 g, 2.95 mmol) furnished the product (517 mg, 67%).

¹H-n.m.r. (CDCl₃) δ 1.59 (d, J=6.9 Hz, 3H, CH₃), 3.81 (s, 3H, OCH₃), 4.87 (m, 1H, CH), 5.47 (br s, 1H, NH), 6.79–7.30 (m, 4H, Ar—H), 7.66 (s, 1H, pyraz-H), 7.79 (s, 1H, pyraz-H).

EXAMPLE 4

2-Methoxy-4-(6-{[(1R)-1-(3-methoxyphenyl)ethyl]amino}pyrazin-2-yl)phenol

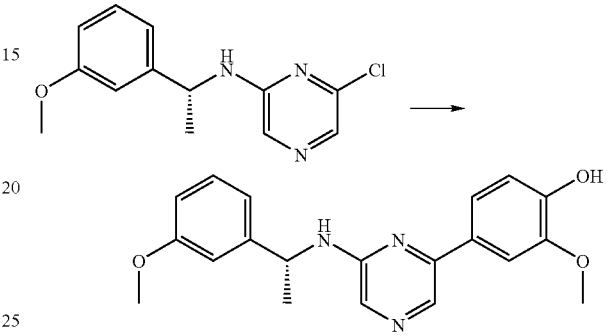

In a procedure analogous to Example 2, reaction of 2-(R-α-methyl-3-methoxy-benzylamino)-6-chloro-pyrazine (137.2 mg, 0.52 mmol) and 2-methoxy-4-(4,4,5,5-tetramethyl-1,3,2-dioxaborolan-2-yl)phenol (143 mg, 0.57 mmol) furnished the product (32 mg, 18%).

¹H-n.m.r. (CDCl₃) δ 1.61 (d, J=6.6 Hz, 3H, CH₃), 3.79 (s, 3H, OCH₃), 3.94 (s, 3H, OCH₃), 4.94 (m, 1H, CH), 5.02 (d, J=6 Hz, 1H, NH), 6.04 (br s, 1H, OH), 6.77–7.48 (m 7H, Ar—H), 7.69 (s, 1H, pyraz-H), 8.23 (s, 1H, pyraz-H)

m/z (ES) 352 (M⁺+H).

EXAMPLE 5

6-Chloro-N-[(1R)-1-(4-methoxyphenyl)ethyl]pyrazin-2-amine

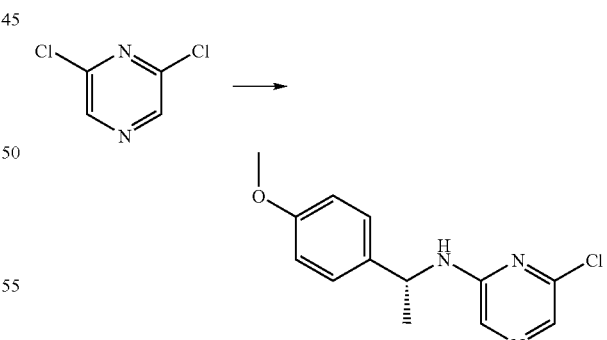

In a procedure analogous to Example 1, reaction of R-α-methylbenzylamine (1.0 g, 6.6 mmol) and 2,6-dichloropyrazine (0.4355 g, 2.92 mmol) furnished the product (0.72 g, 93%).

¹H-n.m.r. (CDCl₃) δ 1.56 (d, 3H, J=6.9 Hz, CH₃), 3.80 (s, 3H, OCH₃), 4.84 (m, 1H, CH), 5.25 (br s, 1H, NH), 6.88 (AA'XX', 2H, Ar—H), 7.28 (AA'XX', 2H, Ar—H), 7.64 (s, 1H, pyraz-H), 7.78 (s, 1H, pyraz-H).

EXAMPLE 6

2-Methoxy-4-(6-{[(1R)-1-(4-methoxyphenyl)ethyl]amino}pyrazin-2-yl)phenol

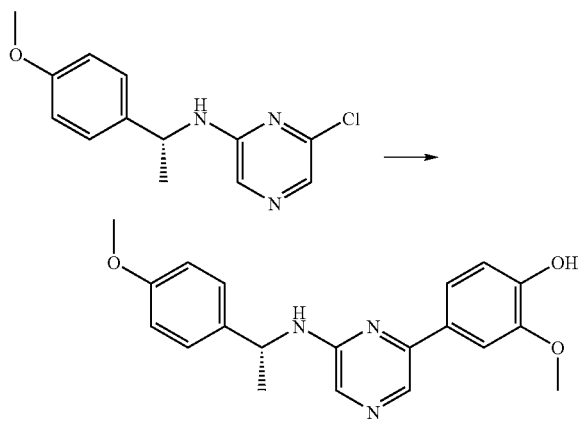

In a procedure analogous to Example 2, reaction of 2-(R-α-methyl-4-methoxy-benzylamino)-6-chloro-pyrazine (127.1 mg, 0.48 mmol) and 2-methoxy-4-(4,4,5,5-tetramethyl-1,3,2-dioxaborolan-2-yl)phenol (145 mg, 0.58 mmol) furnished the product (59.5 mg, 35%).

$^1$H-n.m.r. (CDCl$_3$) δ 1.59 (d, 3H, J=6.6 Hz, CH$_3$), 3.79 (s, 3H, OCH$_3$), 3.95 (s, 3H, OCH$_3$), 4.97 (m, 2H, CH and NH), 5.95 (br s, 1H, OH), 6.87 (AA'XX', 2H, ArH), 6.97 (d, 1H, J=8.1 Hz, ArH), 7.32 (AA'XX', 2H, Ar—H), 7.46 (m, 2H, ArH), 7.66 (s, 1H, pyraz-H), 8.22 (s, 1H, pyraz-H).

m/z (ES) 352 (M$^+$+H).

EXAMPLE 7

6-Chloro-N-[(1R)-1,2,3,4-tetrahydronaphthalen-1-yl]pyrazin-2-amine

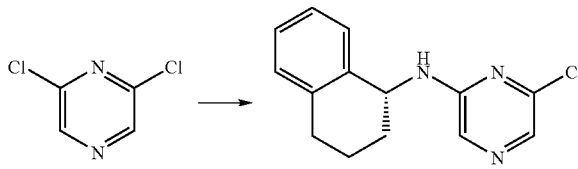

In a procedure analogous to Example 1, reaction of (1R)-1,2,3,4-tetrahydronaphthalen-1-amine (441 mg, 3.0 mmol) and 2,6-dichloropyrazine (0.4055 g, 2.72 mmol) furnished the product (521 mg, 74%).

$^1$H-n.m.r. (CDCl$_3$) δ 1.89 (m, 2H, CH$_2$CH$_2$Ar), 1.97 (m, 1H, H—CHCH$_2$CH$_2$Ar), 2.08 (m, 1H, HC—H—CH$_2$CH$_2$Ar), 2.83 (m, 2H, CH$_2$Ar), 4.94 (br s, 1H, NH), 5.15 (m, 1H, CH), 7.12–7.31 (m, 4H, Ar—H), 7.76 (s, 1H, pyraz-H), 7.81 (s, 1H, pyraz-H).

EXAMPLE 8

2-Methoxy-4-{6-[(1R)-1,2,3,4-tetrahydronaphthalen-1-ylamino]pyrazin-2-yl}phenol

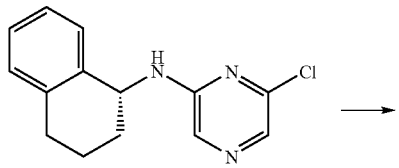

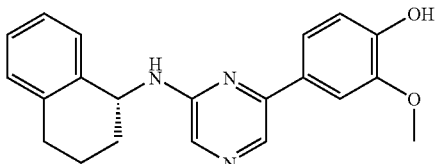

In a procedure analogous to Example 2, reaction of 6-chloro-N-[(1R)-1,2,3,4-tetrahydronaphthalen-1-yl]pyrazin-2-amine (139 mg, 0.536 mmol) and 2-methoxy-4-(4,4,5,5-tetramethyl-1,3,2-dioxaborolan-2-yl)phenol (147 mg, 0.59 mmol) furnished the product (87 mg, 47%).

$^1$H-n.m.r. (CDCl$_3$) δ 1.91 (m, 2H, CH$_2$CH$_2$Ar), 2.09 (m, 2H, CH$_2$CH$_2$CH$_2$Ar), 2.85 (m, 2H, CH$_2$Ar), 3.96 (s, 3H, OCH$_3$), 4.87 (d, J=7.8 Hz, 1H, NH), 5.28 (m, 1H, CH), 6.04 (br s, 1H, OH), 6.98–7.73 (m, 7H, Ar—H), 7.79 (s, 1H, pyraz-H), 8.26 (s, 1H, pyraz-H).

m/z (ES) 348 (M$^+$+H).

EXAMPLE 9

6-Chloro-N-[(1R)-2,3-dihydro-1H-inden-1-yl]pyrazin-2-amine

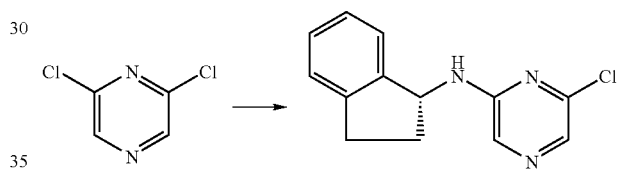

In a procedure analogous to Example 1, reaction of (1)-2,3-dihydro-1H-inden-1-ylamine (1.0 g, 7.6 mmol) and 2,6-dichloropyrazine (0.452 g, 3.04 mmol) furnished the product (673.8 mg, 90%).

$^1$H-n.m.r. (CDCl$_3$) δ 1.91 (m, 1H, H—CHCH$_2$Ar), 2.68 (m, 1H, HC—H—CHCH$_2$Ar), 3.00 (m, 2H, CH$_2$Ar), 5.03 (br s, 1H, NH), 5.45 (m, 1H, CH), 7.18–7.33 (m, 4H, Ar—H), 7.82 (br s, 2H, 2×pyraz-H).

EXAMPLE 10

4-{6-[(1R)-2,3-Dihydro-1H-inden-1-ylamino]pyrazin-2-yl}-2-methoxyphenol

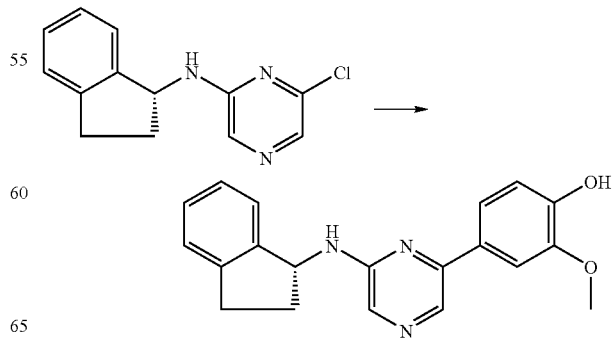

In a procedure analogous to Example 2, reaction of 6-chloro-N-[(1R)-2,3-dihydro-1H-inden-1-yl]pyrazin-2-amine (136.8 mg, 0.56 mmol) and 2-methoxy-4-(4,4,5,5-tetramethyl-1,3,2-dioxaborolan-2-yl)phenol (153 mg, X0.61 mmol) furnished the product (130 mg, 70%).

$^1$H-n.m.r. (CDCl$_3$) δ 2.00 (m, 1H, HC—H—CH$_2$Ar), 2.71 (m, 1H, H—CHCH$_2$Ar), 3.01 (m, 2H, CH$_2$Ar), 3.96 (s, 3H, OCH$_3$), 4.90 (d, J=7.8 Hz, 1H, NH), 5.57 (m, 1H, CH), 6.06 (br s, 1H, OH), 6.98–7.82 (m, 7H, Ar—H), 7.85 (s, 1H, pyraz-H), 8.29 (s, 1H, pyraz-H);

m/z(ES) 334 (M$^+$+H).

EXAMPLE 11

6-Chloro-N-[(1R)-1-(4-methylphenyl)ethyl]pyrazin-2-amine

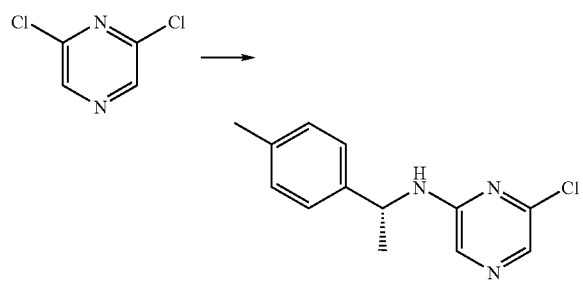

In a procedure analogous to Example 1, reaction of α-(R)-4-dimethylbenzylamine (250 mg, 1.85 mmol) and 2,6-dichloropyrazine (0.251 g, 1.67 mmol) furnished the product (199.5 mg, 48%).

$^1$H-n.m.r. (CDCl$_3$) δ 1.56 (d, 3H, J=6.9 Hz, CH$_3$), 2.33 (s, 3H, CH$_3$), 4.84 (m, 1H, CH), 5.05 (br s, 1H, NH), 7.15 (AA'XX', 2H, Ar—H), 7.24 (AA'XX', 2H, Ar—H), 7.60 (s, 1H, pyraz-H), 7.78 (s, 1H, pyraz-H).

EXAMPLE 12

2-Methoxy-4-(6-{[(1R)-1-(4-methylphenyl)ethyl]amino}pyrazin-2-yl)phenol

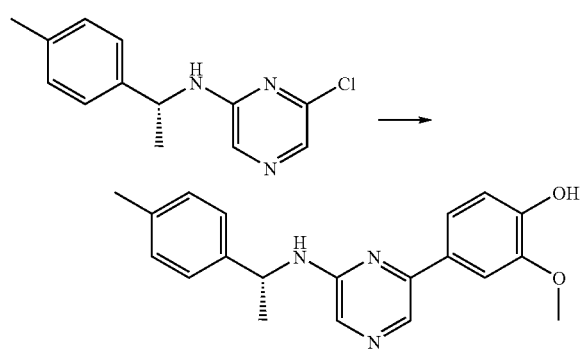

In a procedure analogous to Example 2, reaction of 6-chloro-N-[(1R)-1-(4-methylphenyl)ethyl]pyrazin-2-amine (56.8 mg, 0.229 mmol) and 2-methoxy-4-(4,4,5,5-tetramethyl-1,3,2-dioxaborolan-2-yl)phenol 63 mg, 0.25 mmol) furnished the product (5 mg, 6%).

$^1$H-n.m.r. (CDCl$_3$) δ 1.60 (d, 3H, J=6.6 Hz, CH$_3$), 2.33 (s, 3H, CH$_3$), 3.95 (s, 3H, OCH$_3$), 4.96 (m, 2H, CH and NH), 5.89 (br s, 1H, OH), 6.97 (d, 1H, J=8.4 Hz, ArH), 7.14 (AA'XX', 2H, ArH), 7.30 (AA'XX', 2H, Ar—H), 7.42–7.48 (m, 2H, Ar—H), 7.67 (s, 1H, pyraz-H), 8.62 (s, 1H, pyraz-H).

m/z (ES) 336 (M$^+$+H).

EXAMPLE 13

6-Chloro-N-[(1S)-1-phenylethyl]pyrazin-2-amine

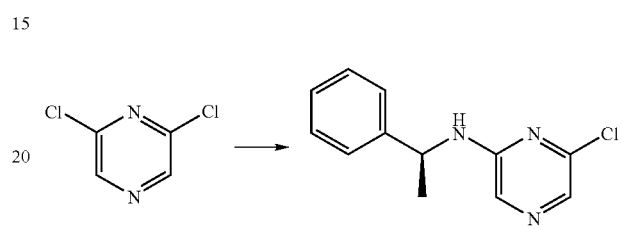

In a procedure analogous to Example 1, reaction of S-α-methylbenzylamine (568.8 mg, 4.72 mmol) and 2,6-dichloropyrazine (0.6388 g, 4.29 mmol) furnished the product (821 mg, 82%).

$^1$H-n.m.r. (CDCl$_3$) δ 1.58 (d, J=6.6 Hz, 3H, CH$_3$), 4.88 (m, 1H, CH), 5.07 (d, 1H, NH), 7.24–7.36 (m, 5H, Ar—H), 7.61 (s, 1H, pyraz-H), 7.79 (s, 1H, pyraz-H).

EXAMPLE 14

2-Methoxy-4-(6-{[(1S)-1-phenylethyl]amino}pyrazin-2-yl)phenol

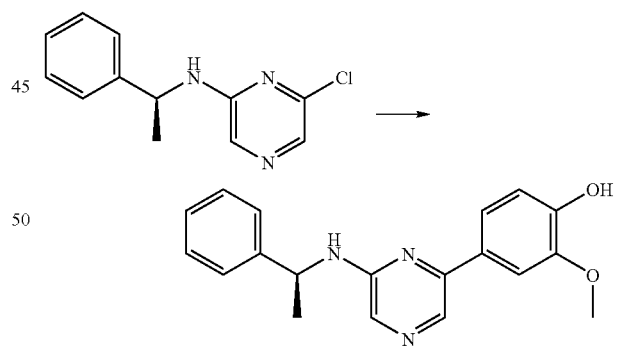

In a procedure analogous to Example 2, reaction of 6-chloro-N-[(1S)-1-phenylethyl]pyrazin-2-amine (717.3 mg, 3.07 mmol) and 2-methoxy-4-(4,4,5,5-tetramethyl-1,3,2-dioxaborolan-2-yl)phenol (845 mg, 3.38 mmol) furnished the product (689 mg, 70%).

$^1$H-n.m.r. (CDCl$_3$) δ 1.63 (d, 3H, J=6.6 Hz, CH$_3$), 3.95 (s, 3H, OCH$_3$), 4.99 (m, 2H, CH+NH), 5.74 (br s, 1H, OH), 6.97 (d, 1H, J=8.1 Hz, Ar—H), 7.24–7.46 (m, 7H, Ar—H), 7.69 (s, 1H, pyraz-H), 8.23 (s, 1H, pyraz-H).

EXAMPLE 15

6-Chloro-N-[(1S)-1-phenylpropyl]pyrazin-2-amine

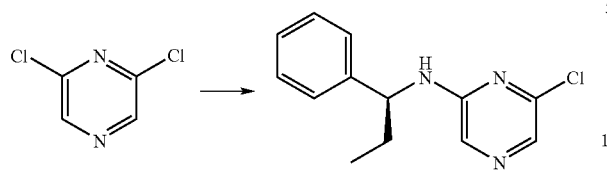

In a procedure analogous to Example 1, reaction of S-α-ethylbenzylamine (558 mg, 4.21 mmol) and 2,6-dichloropyrazine (570 mg, 3.82 mmol) furnished the product (655 mg, 73%).

$^1$H-n.m.r. (CDCl$_3$) δ 0.96 (t, 3H, CH$_3$), 1.90 (m, 2H, CH$_2$), 4.59 (m, 1H, CH), 5.12 (d, 1H, NH), 7.24–7.37 (m, 5H, Ar—H), 7.60 (s, 1H, pyraz-H), 7.78 (s, 1H, pyraz-H).

EXAMPLE 16

2-Methoxy-4-(6-{[(1S)-1-phenylpropyl]amino}pyrazin-2-yl)phenol

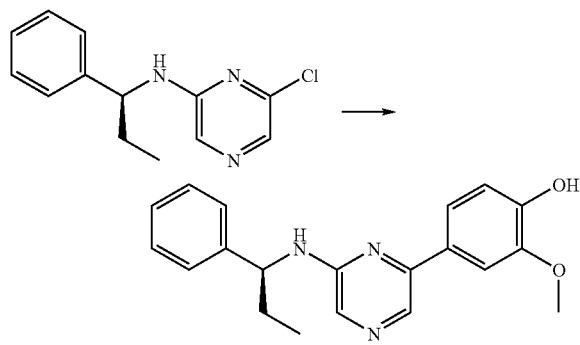

In a procedure analogous to Example 2, reaction of 6-chloro-N-[(1S)-1-phenylpropyl]pyrazin-2-amine (135 mg, 0.57 mmol) and 2-methoxy-4-(4,4,5,5-tetramethyl-1,3,2-dioxaborolan-2-yl)phenol (158 mg, 0.63 mmol) furnished the product (87 mg, 45%).

$^1$H-n.m.r. (CDCl$_3$) δ 1.00 (t, 3H, J=7.5 Hz, CH$_3$), 1.94 (dq, 2H, J=7.5 Hz, CH$_2$), 3.96 (s, 3H, OCH$_3$), 4.71 (dt, 1H, J=7.5 Hz, CH), 5.00 (br s, 1H, NH), 5.75 (br s, 1H, OH), 6.97 (d, 1H, J=8.4 Hz, ArH), 7.24 (m, 1H, ArH), 7.30–7.47 (m, 6H, ArH), 7.67 (s, 1H, pyraz-H), 8.21 (s, 1H, pyraz-H).

m/z (ES) 336 (M$^+$+H).

EXAMPLE 17

(2R)-2-[(6-Chloropyrazin-2-yl)amino]-2-phenylethanol

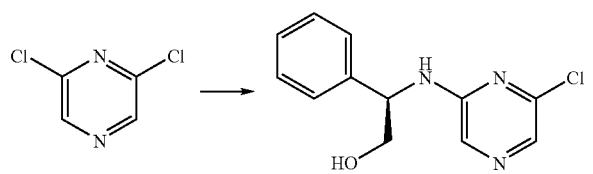

In a procedure analogous to Example 1, reaction of (2R)-2-amino-2-phenylethanol (420 mg, 3.1 mmol) and 2,6-dichloropyrazine (415 mg, 2.79 mmol) furnished the product (261 mg, 37%).

$^1$H-n.m.r. (CDCl$_3$) δ 0.91 (d, 1H, OH), 3.97 (m, 2H, CH$_2$), 4.94 (m, 1H, CH), 5.56 (d, 1H, NH), 7.30–7.44 (m, 5H, Ar—H), 7.70 (s, 1H, pyraz-H), 7.81 (s, 1H, pyraz-H).

EXAMPLE 18

4-(6-{[(1R)-2-Hydroxy-1-phenylethyl]amino}pyrazin-2-yl)-2-methoxyphenol

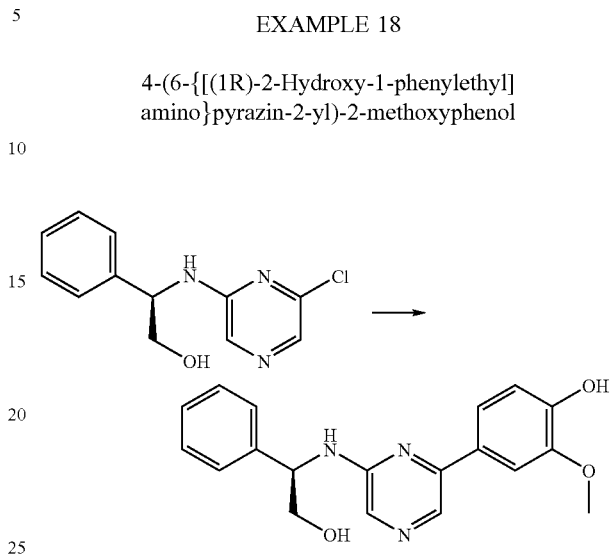

In a procedure analogous to Example 2, reaction of (2R)-2-[(6-chloropyrazin-2-yl)amino]-2-phenylethanol (137 mg, 0.55 mmol) and 2-methoxy-4-(4,4,5,5-tetramethyl-1,3,2-dioxaborolan-2-yl)phenol (151 mg, 0.60 mmol) furnished the product (70 mg, 38%).

$^1$H-n.m.r. (CDCl$_3$) δ 1.16 (s, 1H, OH), 382 (s, 3H, OCH$_3$), 3.90 (m, 2H, CH$_2$), 4.92 (m, 1H, CH), 5.50 (br s, 1H, NH), 6.87 (d, 1H, J=9 Hz, ArH), 7.15–7.66 (m, 8H, ArH), 8.14 (s, 1H, pyraz-H).

m/z (ES) 338 (M$^+$+H).

EXAMPLE 19

6-Chloro-N-[(1S)-1-(4-methoxyphenyl)ethyl]pyrazin-2-amine

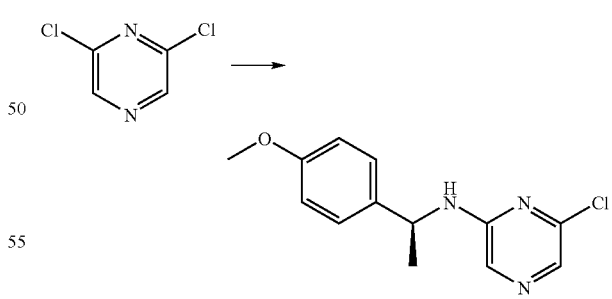

In a procedure analogous to Example 1, reaction of 4-methoxy-α-(S)-methylbenzylamine (0.70 mg, 4.6 mmol) and 2,6-dichloropyrazine (0.6259 g, 4.20 mmol) furnished the product (873 mg, 79%).

$^1$H-n.m.r. (CDCl$_3$) δ 1.56 (d, 3H, J=6.9 Hz, CH$_3$), 3.80 (s, 3H, OCH$_3$), 4.84 (m, 1H, CH), 5.01 (br s, 1H, NH), 6.88 (AA'XX', 2H, Ar—H), 7.28 (AA'XX', 2H, Ar—H), 7.61 (s, 1H, pyraz-H), 7.79 (s, 1H, pyraz-H).

EXAMPLE 20

2-Methoxy-4-(6-{[(1S)-1-(4-methoxyphenyl)ethyl]amino}pyrazin-2-yl)phenol

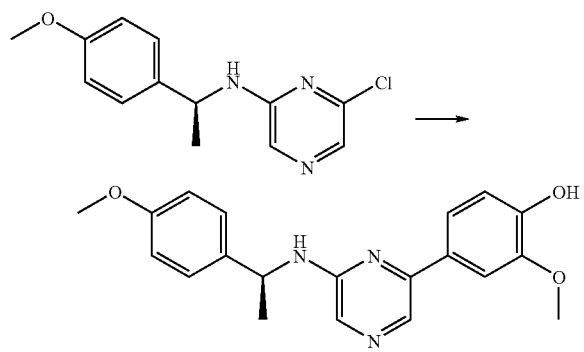

In a procedure analogous to Example 2, reaction of 6-chloro-N-[(1S)-1-(4-methoxyphenyl)ethyl]pyrazin-2-amine (149.4 mg, 0.57 mmol) and 2-methoxy-4-(4,4,5,5-tetramethyl-1,3,2-dioxaborolan-2-yl)phenol (156 mg, 0.62 mmol) furnished the product (71 mg, 35%).

$^1$H-n.m.r. (CDCl$_3$) δ 1.59 (d, 3H, J=6.6 Hz, CH$_3$), 3.79 (s, 3H, OCH$_3$), 3.95 (s, 3H, OCH$_3$), 4.95 (m, 2H, CH and NH), 5.98 (br s, 1H, OH), 6.87 (AA'XX', 2H, ArH), 6.97 (d, 1H, J=8.1 Hz, ArH), 7.33 (AA'XX', 2H, Ar—H), 7.43–7.49 (m, 2H, ArH), 7.66 (s, 1H, pyraz-H), 8.22 (s, 1H, pyraz-H).

m/z (ES) 352 (M$^+$+H).

EXAMPLE 21

6-Chloro-N-(pyridin-3-ylmethyl)pyrazin-2-amine

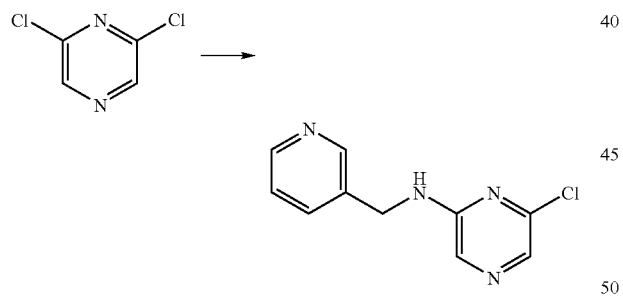

A mixture 2,6-dichloropyrazine (0.671 mmol) and 3-picolylamine (2.014 mmol) in xylene (25 ml) was refluxed overnight. The residue obtained after evaporation of the solvent was suspended between CH$_2$Cl$_2$ (100 ml) and water (100 ml). The organic layer was separated and the aqueous layer was extracted with CH$_2$Cl$_2$ (3×50 ml). The combined organic extracts were washed with brine (1×100 ml), dried (Na$_2$SO$_4$) and the solvent removed in vacuo. The residue was then purified by column chromatography eluting with a hexane:ethyl acetate gradient mixture to afford the desired product (93%).

$^1$H-n.m.r. (CDCl$_3$) δ 4.61 (d, J=5.7 Hz, 2H, NCH$_2$), 5.29 (s, broad, 1H, NH), 7.27 (m, 1H, pyrid.-H), 7.30 (m, 1H, pyrid.-H), 7.71 (d, J=7.8 Hz, 1H, pyrid.-H), 7.85 (s, 1H, pyrid.-H), 8.54 (s, broad, 1H, pyraz.-H), 8.61 (s, broad, 1H, pyraz.-H).

EXAMPLE 22

2-Methoxy-4-{6-[(pyridin-3-ylmethyl)amino]pyrazin-2-yl}phenol

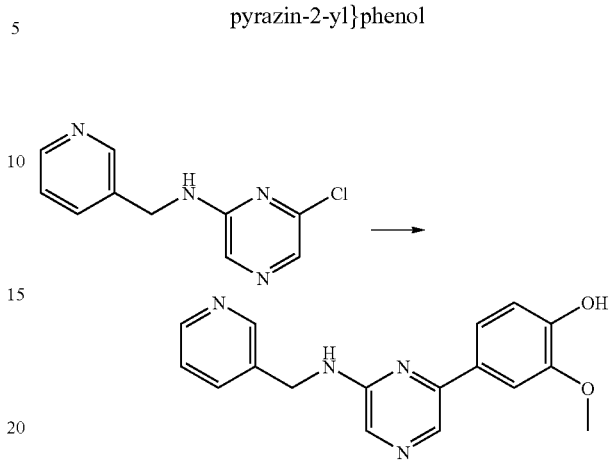

A mixture of 6-chloro-N-(pyridin-3-ylmethyl)pyrazin-2-amine (49 mg, 0.22 mmol), 2-methoxy-4-(4,4,5,5-tetramethyl-1,3,2-dioxaborolan-2-yl)phenol (52 mg, 0.20 mmol), (PPh$_3$)$_4$Pd (23 mg, 0.020 mmol) and a Na$_2$CO$_3$ solution (0.22 mmol of a 2 M solution) in toluene (10 ml) was heated under reflux overnight. After removal of the solvents, the residue was dissolved in CH$_2$Cl$_2$ (150 ml), dried (Na$_2$SO$_4$), filtered and the CH$_2$Cl$_2$ removed in vacuo. The residue was purified by column chromatography, eluting with a n-hexane:ethyl acetate gradient mixture to obtain the desired product (62 mg, 75%).

$^1$H-n.m.r. (CDCl$_3$) δ 3.94 (br s, 3H, CH$_3$), 4.70 (d, 2H, J=6.0 Hz, CH$_2$), 5.01 (br s, 1H, NH), 5.83 (br s, 1H, OH), 6.98 (d, 1H, J=8.7 Hz, ArH), 7.29 (m, 1H, Ar—H), 7.48 (m, 2H, ArH), 7.73 (br d, 1H, J=8.7 Hz, ArH), 7.83 (s, 1H, pyraz-H), 8.30 (s, 1H, pyraz-H), 8.54 (m, 1H, ArH), 8.70 (s, 1H, ArH).

m/z (ES) 309 (M$^+$+H).

EXAMPLE 23

N-Benzyl-6-chloro-N-methylpyrazin-2-amine

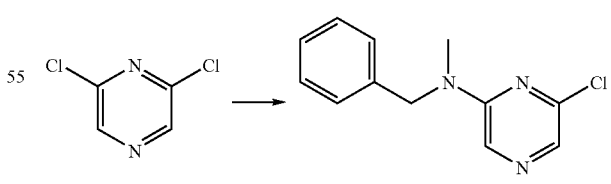

In a procedure analogous to Example 21, reaction of N-methyl benzylamine and 2,6-dichloropyrazine furnished the product (70%).

$^1$H-n.m.r. (CDCl$_3$) δ 3.11 (s, 3H, NCH$_3$), 4.78 (s, 2H, ArCH$_2$N), 7.24 (d, J=6.9 Hz, 2H, ArH), 7.37–7.28 (m, 4H, ArH), 7.81 (s, 1H, pyraz.-H), 7.88 (s, 1H, pyraz.-H).

EXAMPLE 24

4-{6-[Benzyl(methyl)amino]pyrazin-2-yl}-2-methoxyphenol

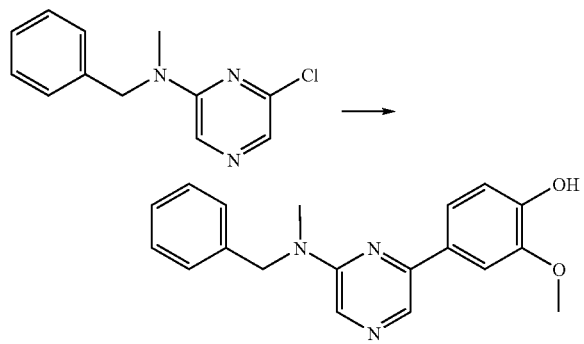

In a procedure analogous to Example 22, reaction of N-benzyl-6-chloro-N-methylpyrazin-2-amine and 2-methoxy-4-(4,4,5,5-tetramethyl-1,3,2-dioxaborolan-2-yl)phenol furnished the product (51%).

$^1$H-n.m.r. (CDCl$_3$) δ 3.20 (br s, 3H, NCH$_3$), 3.91 (s, 3H, OCH$_3$), 4.89 (s, 2H, CH$_2$), 5.83 (br s, 1H, OH), 6.98 (d, 1H, J=8.1 Hz, ArH), 7.27 (m, 5H, Ar—H), 7.53 (m, 2H, ArH), 7.93 (s, 1H, pyraz.-H), 8.28 (s, 1H, pyraz.-H).

m/z (ES) 322 (M$^+$+H).

EXAMPLE 25

2-(6-Chloropyrazin-2-yl)-1,2,3,4-tetrahydroisoquinoline

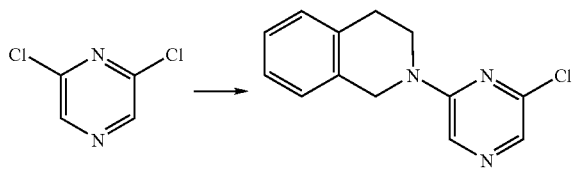

In a procedure analogous to Example 21, reaction of tetrahydroisoquinoline and 2,6-dichloropyrazine furnished the product (95%).

$^1$H-n.m.r. (CDCl$_3$) δ 2.99 (t, J=5.7 Hz, 2H, ArCH$_2$CH$_2$N), 3.86 (t, J=5.7 Hz, 2H, ArCH$_2$CH$_2$N), 4.73 (s, 2H, ArCH$_2$N), 7.27–7.19 (m, 4H, ArH), 7.82 (s, 1H, pyraz.-H), 8.01 (s, 1H, pyraz.-H).

EXAMPLE 26

4-[6-(3,4-Dihydroisoquinolin-2(1H)-yl)pyrazin-2-yl]-2-methoxyphenol

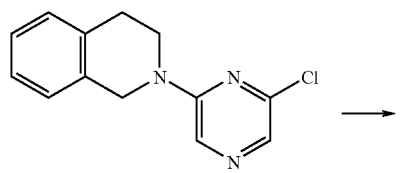

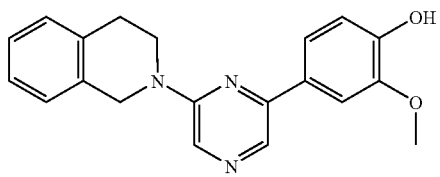

In a procedure analogous to Example 22, reaction of 2-(6-chloropyrazin-2-yl)-1,2,3,4-tetrahydroisoquinoline and 2-methoxy-4-(4,4,5,5-tetramethyl-1,3,2-dioxaborolan-2-yl)phenol furnished the product (44%).

$^1$H-n.m.r. (CDCl$_3$) δ 3.03 (m, 2H, CH$_2$), 3.96 (m, 2H, CH$_2$), 4.01 (s, 3H, OCH$_3$), 4.83 (s, 2H, CH$_2$), 5.87 (br s, 1H, OH), 7.04 (m, 1H, ArH), 7.21 (m, 3H, Ar—H), 7.56 (m, 2H, ArH), 8.07 (br s, 1H, pyraz.-H), 8.28 (br s, 1H, pyraz.-H).

m/z (ES) 374 (M+H+K)$^+$.

EXAMPLE 27

6-Chloro-N-(3,4-dichlorobenzyl)pyrazin-2-amine

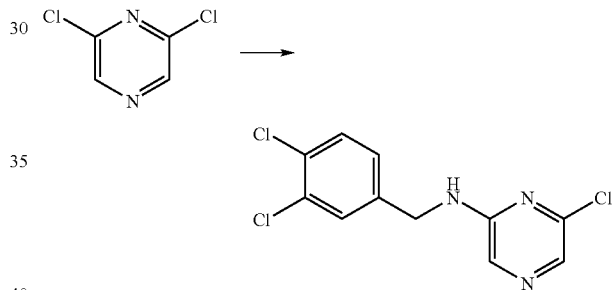

In a procedure analogous to Example 21, reaction of 3,4-dichlorobenzylamine and 2,6-dichloropyrazine furnished the product (89%).

$^1$H-n.m.r. (CDCl$_3$) δ 4.55 (d, J=6 Hz, 2H, NCH$_2$), 5.01 (s, broad, 1H, NH), 7.18 (dd, J=2.1, 2.1 Hz, 1H, ArH), 7.20 (dd, J=2.1, 2.1 Hz, 1H, ArH), 7.45–7.41 (m, 2H, ArH), 7.77 (s, 1H, pyraz.-H), 7.86 (s, 1H, pyraz.-H).

EXAMPLE 28

4-{6-[(3,4-Dichlorobenzyl)amino]pyrazin-2-yl}-2-methoxyphenol

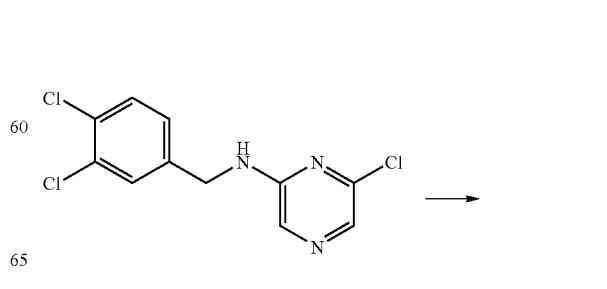

-continued

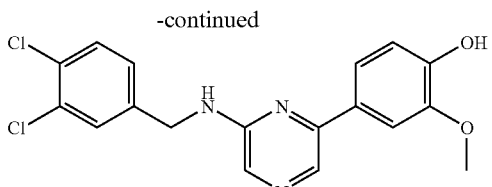

In a procedure analogous to Example 22, reaction of 6-chloro-N-(3,4-dichlorobenzyl)pyrazin-2-amine and 2-methoxy-4-(4,4,5,5-tetramethyl-1,3,2-dioxaborolan-2-yl)phenol furnished the product (57%).

¹H-n.m.r. (CDCl₃) δ 3.93 (s, 3H, CH₃), 4.62 (d, 2H, J=6.0 Hz, CH₂), 5.01 (br s, 1H, NH), 5.79 (br s, 1H, OH), 6.98 (d, 1H, J=8.7 Hz, ArH), 7.45 (m, 4H, ArH), 7.68 (m, 1H, ArH), 7.95 (s, 1H, pyraz.-H), 8.29 (s, 1H, pyraz.-H).

m/z (ES) 376 (M⁺).

EXAMPLE 29

6-Chloro-N-(3,5-dimethoxybenzyl)pyrazin-2-amine

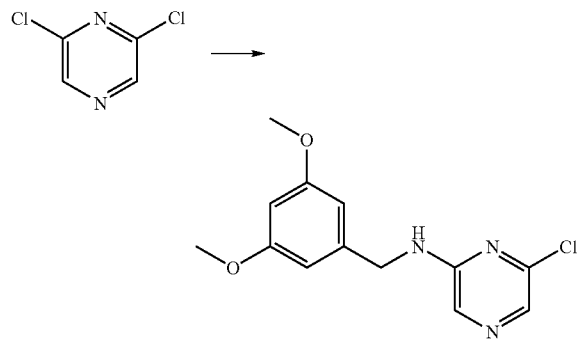

In a procedure analogous to Example 21, reaction of 3,5-dimethoxybenzylamine and 2,6-dichloropyrazine furnished the product (91%).

1H-n.m.r. (CDCl₃) δ 3.78 (s, 6H, OCH₃), 4.49 (d, J=5.4 Hz, 2H, NCH₂), 5.12 (br s, 1H, NH), 6.39 (t, J=2.1 Hz, 1H, ArH), 6.50 (d, J=2.1 Hz, 2H, ArH), 7.75 (s, 1H, pyraz.-H), 7.82 (s, 1H, pyraz.-H).

EXAMPLE 30

4-{6-[(3,5-Dimethoxybenzyl)amino]pyrazin-2-yl}-2-methoxyphenol

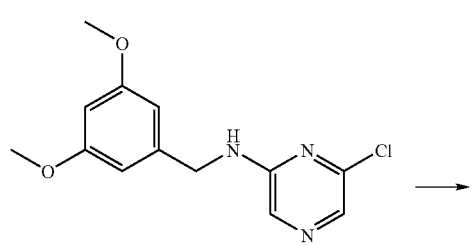

-continued

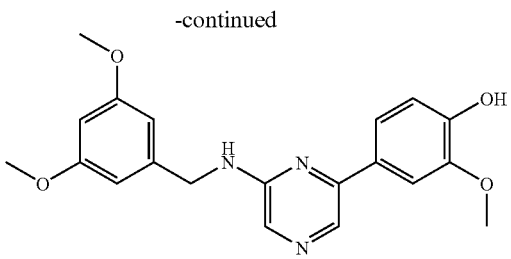

In a procedure analogous to Example 22, reaction of 6-chloro-N-(3,5-dimethoxybenzyl)pyrazin-2-amine and 2-methoxy-4-(4,4,5,5-tetramethyl-1,3,2-dioxaborolan-2-yl)phenol furnished the product (88%).

¹H-n.m.r. (as mesylate salt) (d6-DMSO) δ 2.39 (s, 3H, CH₃SO₃), 3.69 (s, 6H, OCH₃), 3.80 (s, 3H, OCH₃), 4.51 (s, 2H, CH₂), 6.36 (d, 1H, J=2.1 Hz, ArH), 6.57 (d, 2H, J=2.1 Hz, ArH), 6.83 (d, 1H, J=8.1 Hz, ArH), 7.54 (m, 2H, ArH), 7.87 (s, 1H, pyraz-H), 8.29 (s, 1H, pyraz-H).

m/z (ES) 368 (M⁺+H).

EXAMPLE 31

6-Chloro-N-(2-furylmethyl)pyrazin-2-amine

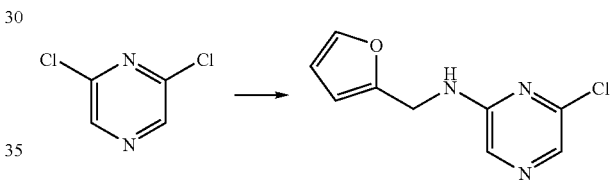

In a procedure analogous to Example 21, reaction of furfurylamine and 2,6-dichloropyrazine furnished the product (98%).

¹H-n.m.r. (CDCl₃) δ 4.57 (d, J=5.7 Hz, 2H, NCH₂), 5.01 (s, broad, 1H, NH), 6.30 (d, J=3.3 Hz, 1H, furanyl-H), 6.35–6.33 (m, 2H, furanyl-H), 7.81 (s, 1H, pyraz.-H), 7.84 (s, 1H, pyraz.-H).

EXAMPLE 32

4-{6-[(2-Furylmethyl)amino]pyrazin-2-yl}-2-methoxyphenol

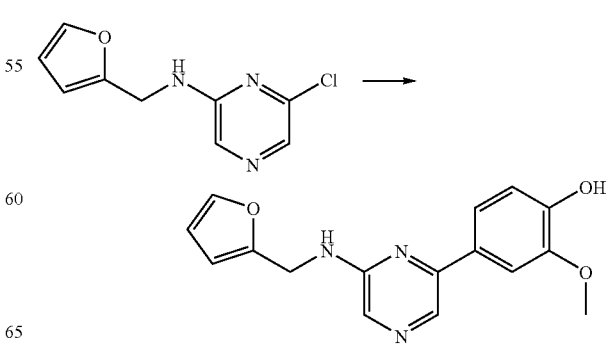

In a procedure analogous to Example 2, reaction of 6-chloro-N-(2-furylmethyl)pyrazin-2-amine and 2-methoxy-4-(4,4,5,5-tetramethyl-1,3,2-dioxaborolan-2-yl)phenol furnished the product (92%).

$^1$H-n.m.r. (as mesylate salt) (d6-DMSO) δ 2.38 (s, 3H, CH$_3$SO$_3$), 3.84 (s, 3H, OCH$_3$), 4.59 (s, 2H, CH$_2$), 6.33 (s, 1H, ArH), 6.38 (s, 1H, ArH), 6.87 (d, 2H, J=8.1 Hz, ArH), 7.52 (m, 3H, ArH), 7.86 (br s, 1H, pyraz.-H), 8.30 (br s, 1H, pyraz.-H).

m/z (ES) 298 (M$^+$+H).

EXAMPLE 33

2-Chloro-4-(6-{[(1S)-1-phenylethyl]amino}pyrazin-2-yl)phenol

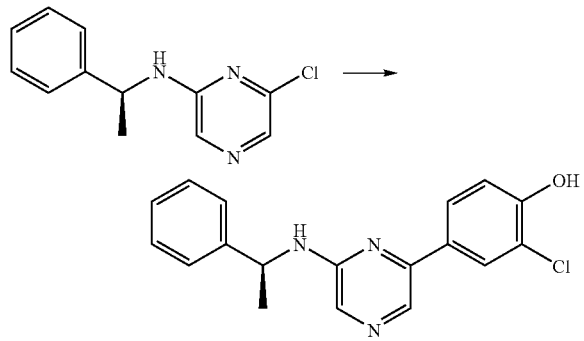

A solution of 4-bromo-2-chlorophenol (246 mg, 1.18 mmol), bis(pinacolato)diboron (332 mg, 1.3 mmol), [1,1'-bis(diphenylphosphino)ferrocene]palladium(II) chloride (26 mg, 0.035 mmol) and potassium acetate (222 mg, 2.26 mmol) in dry methanol (4 mL) was degassed and heated at 65° C. for 24 h. After cooling, the reaction mixture was diluted with ether and filtered through Celite. The solvent was removed under reduced pressure and the residue purified by chromatography using dichloromethane-hexane (90:10) as eluant. The boronate thus obtained (50 mg) was reacted with 6-chloro-N-[(1S)-1-phenylethyl]pyrazin-2-amine (50 mg, 0.2 mmol) under conditions analogous to those of example 2, to furnish the pure product after chromatography eluting with dichloromethane-ether (90:10) (44 mg, 68%).

$^1$H-n.m.r. δ δ 1.59 (d, 3H, J=6.0 Hz, CH$_3$), 4.88 (m, 1H, CH), 5.08 (br s, 1H, NH), 5.69 (br s, 1H, NH), 7.07 (d, 1H, J=8.5 Hz, ArH), 7.27–7.36 (m, 6H, Ar—H), 7.48 (d, 1H, J=1.5 Hz, ArH), 7.62 (s, 1H, pyraz-H), 7.80 (s, 1H, pyraz-H).

EXAMPLE 34

6-(4-Aminophenyl)-N-[(1S)-1-phenylethyl]pyrazin-2-amine

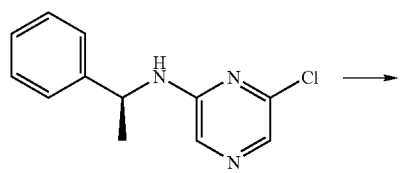

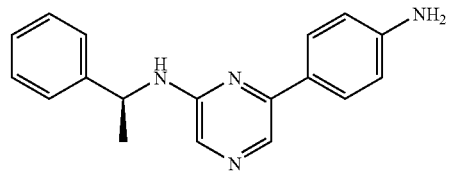

A mixture of 6-chloro-N-[(1S)-1-phenylethyl]pyrazin-2-amine (1.10 g, 4.71 mmol), 4-(4,4,5,5-tetramethyl-1,3,2-dioxaborolan-2-yl) aniline (1.10 g, 5.02 mmol), (PPh$_3$)$_4$Pd (580 mg, 0.5 mmol) and a Na$_2$CO$_3$ solution (2.6 ml, 2M solution) in toluene (20 ml) was heated under reflux for 40 h. Upon cooling, the mixture was diluted with water (30 mL) and the product extracted with ethyl acetate (3×40 ml). The organic layers were combined, washed with brine (30 ml), dried (Na$_2$SO$_4$), and the solvent removed in vacuo. The residue was purified by column chromatography, eluting with a hexane-ethyl acetate (2:3) to furnish the desired product from the polar fractions (0.86 g, 63%).

$^1$H-n.m.r. (CDCl$_3$) δ 1.57 (d, 3H, J=6.2 Hz, CH$_3$), 3.80 (br s, 2H, NH$_2$), 4.92–4.99 (m, 2H, CH$^-$+NH), 6.69 (d, 2H, J=6.7 Hz, ArH), 7.21–7.40 (m, 5H, ArH), 7.72 (d, 2H, J=6.7 Hz, ArH), 7.57 (s, 1H, pyraz.-H), 8.16 (s, 1H, pyraz.-H).

m/z (ES) 291 (M$^+$+H)

EXAMPLE 35

6-[4-(Ethylamino)phenyl]-N-[(1S)-1-phenylethyl]pyrazin-2-amine

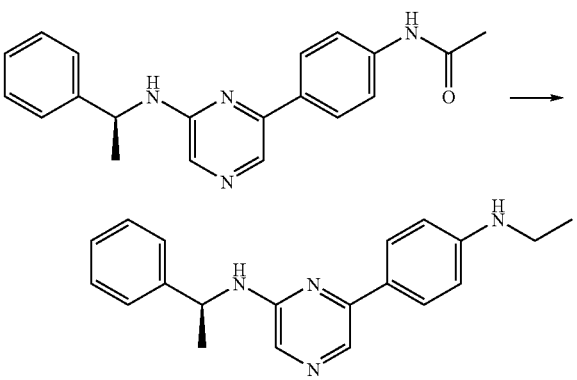

A solution of the amide (40 mg, 0.12 mmol) in THF (5 mL) was treated with solid LiAlH$_4$ (38 mg, 1 mmol), and the mixture stirred at RT for 4 h. The reaction was then treated sequentially with H$_2$O (5 ml), 2M NaOH (5 ml) and water (10 ml) and the resulting suspension then extracted with ethyl acetate (3×15 ml). The combined organic layers were dried (Na$_2$SO$_4$) and concentrated under reduced pressure. The crude product thus obtained was purified by column chromatography using ethyl acetate-hexane (3:1) as eluant to give the product as a colorless solid (22 mg, 58%).

$^1$H-n.m.r. (CDCl$_3$) δ 1.25 (t, 3H, J=7.0 Hz, CH$_3$), 1.57 (d, 3H, J=6.8 Hz, CH$_3$), 3.18 (q, 2H, J=7.0 Hz, CH$_2$), 3.74 (br s. 1H, NH), 4.85–5.01 (m, 2H, CH+NH), 6.59–6.63 (m, 2H, ArH), 7.21–7.40 (m, 5H, ArH), 7.54 (s, 1H, pyraz.-H), 7.73–7.77 (m, 2H, ArH), 8.16 (s, 1H, pyraz.-H).

m/z (ES) 319 (M$^+$+H)

EXAMPLE 36

N-[4-(6-{[(1S)-1-phenylethyl]amino}pyrazin-2-yl)phenyl]methanesulfonamide

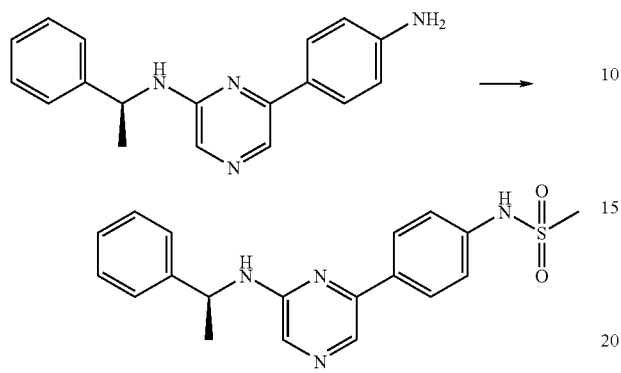

To a stirred solution of 6-(4-aminophenyl)-N-[(1S)-1-phenylethyl]pyrazin-2-amine (58 mg, 0.2 mmol) in dry THF (3 mL) was added triethylamine (70 µL, 0.5 mmol). The solutions was cooled to 0° C. and methanesulphonyl chloride (18.6 µL, 0.24 mmol) was added dropwise. The mixture was allowed to warm to RT and stirred overnight, before dilution with water (15 mL). The product was extracted into ethyl acetate (2×15 mL) and the combined extracts washed with 10% aqueous $Na_2CO_3$ and brine, and then dried ($Na_2SO_4$). The solvent was removed under reduced pressure and the product purified by chromatography eluting with ethyl acetate-hexane (3:2) to afford the product as a pale yellow solid (54 mg, 73%).

$^1$H-n.m.r. ($CDCl_3$) δ 1.59 (d, 3H, J=6.2 Hz, $CH_3$), 3.01 (s, 3H, $CH_3$), 4.96–5.01 (m, 2H, CH+NH), 6.52 (br s, 1H, $NHSO_2$), 7.22–7.40 (m, 7H, ArH), 7.70 (s, 1H, pyraz.-H), 7.85–7.89 (m, 2H, ArH), 8.20 (s, 1H, pyraz.-H).

m/z (ES) 369 ($M^+$+H).

EXAMPLE 37

N-[4-(6-{[(1S)-1-phenylethyl]amino}pyrazin-2-yl)phenyl]cyclopropanecarboxamide

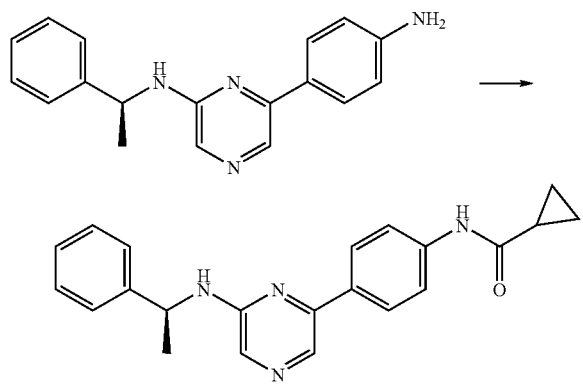

In a method analogous to that reported in example 39, reaction of 6-(4-aminophenyl)-N-[(1S)-1-phenylethyl]pyrazin-2-amine (58 mg, 0.2 mmol) and cyclopropanecarbonyl chloride (25 mg, 0.24 mmol) furnished the pure product after chromatographic purification using ethyl acetate-hexane (3:2) (46 mg, 64%).

$^1$H-n.m.r. ($CDCl_3$) δ 0.82–0.88 (m, 2H, $CH_2$), 1.05–1.10 (m, 2H, $CH_2$), 1.49–1.60 (m, 4H, CH, $CH_3$), 4.91–4.9 (m, 2H, CH+NH), 7.23–7.40 (m, 5H, ArH), 7.56 (AA'XX', 2H, ArH), 7.65 (s, 1H, pyraz.-H), 7.85 (AA'XX', 2H, ArH), 8.21 (s, 1H, pyraz.-H).

m/z (ES) 359 ($M^+$+H).

EXAMPLE 38

1-Pyridin-3-ylethanone oxime

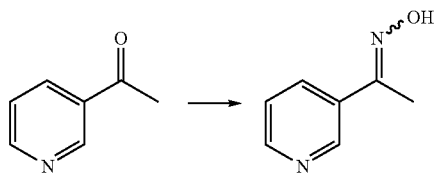

To a solution of hydroxylamine hydrochloride (3.44 g) in water (20 ml) was added NaOH (20%, 30 ml). The ketone (5 g, 41 mmol) was added at once and the resulting mixture was stirred at RT until TLC showed no ketone remained. The solvents were distilled off in vacuo and the residue extracted with $CH_2Cl_2$ (3×100 ml) and dried ($Na_2SO_4$). After filtration and removal of the solvent, the crude ketoxime was recrystallised from $CH_2Cl_2$/n-hexane.

$^1$H-n.m.r. ($CDCl_3$) δ 2.31 (s, 3H, $CH_3$), 7.33 (dd, J=4.8, 4.8 Hz, 1H, ArH), 7.97 (ddd, J=8.1, 1.8, 1.8 Hz, 1H, ArH), 8.61 (dd, J=5.1, 1.8 Hz, 1H, ArH), 8.96 (d, J=1.8 Hz, 1H, ArH), 10.62 (s, 1H, OH).

EXAMPLE 39

1-(3-Chlorophenyl)ethanone oxime

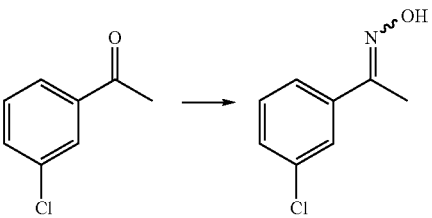

A mixture of the ketone (2.0 g, 13 mmol), hydroxylamine hydrochloride (0.98 g, 14 mmol), NaOH (10%, 4 ml), water (6.2 ml) and EtOH (25 ml) was heated under reflux for 2 hours. Upon cooling in ice, the ketoxime precipitated and was collected by suction filtration. The crude product was recrystallised from $CH_2Cl_2$/n-hexane (1.88 g, 86%).

$^1$H-n.m.r. ($CDCl_3$) δ 2.28 (s, 3H, CH3), 7.51 (s, 4H, ArH), 8.67 (s, 1H, OH).

EXAMPLE 40

1-(3-Chlorophenyl)ethanamine

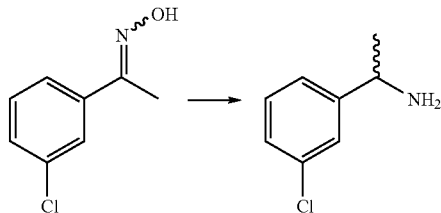

A mixture of the ketoxime (1 g, 6 mmol) and LiAlH$_4$ (0.27 g) in anhydrous THF (100 ml) was heated at reflux under dry N$_2$ overnight. The reaction mixture was cooled in ice-water and carefully quenched with H$_2$O (60 mL). The mixture was allowed to stir at RT for half an hour, after which time it was filtered through Celite®. The inorganic salts were washed with EtOAc (3×100 ml). The filtrate was concentrated under reduced pressure, diluted with 2M HCl (50 ml) and the aqueous phase washed with Et$_2$O (2×70 ml). The aqueous phase was basified with 40% aqueous NaOH and the product extracted with Et$_2$O (3×50 ml). The combined organic layers were washed with brine (50 ml) and dried (MgSO$_4$). The solvents were removed in vacuo to afford the pure amine (0.65 g, 71%).

$^1$H-n.m.r. (CDCl$_3$) δ 1.38 (d, J=6.6 Hz, 3H, CH—CH$_3$), 1.63 (br s, 2H, NH$_2$), 4.13–4.06 (m, 1H, CH—CH$_3$), 7.23–7.18 (m, 3H, ArH), 7.35 (s, 1H, ArH).

EXAMPLE 41

1-Pyridin-3-ylethanamine

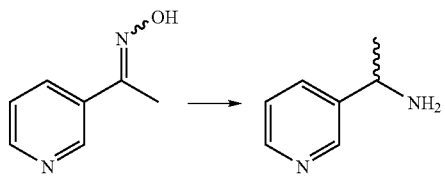

To a mixture of the ketoxime (4.85 g, 36 mmol) and Zn powder (12 g) at 0° C. was slowly added, with vigorous stirring, concentrated HCl (50 ml). When the initial vigorous reaction had subsided, the mixture was heated under reflux until TLC showed all the ketoxime had been consumed. After cooling to RT, the strongly acidic mixture was extracted with CH$_2$Cl$_2$ (2×75 ml). The reaction mixture was then made strongly basic with 50% KOH solution. After removal of the solvent, the residue was extracted with boiling MeOH (4×100 ml). The MeOH was distilled off to leave the crude amine which was used in the ensuing reactions without further purification.

$^1$H-n.m.r. (CDCl$_3$) δ 1.07 (d, J=6.6 Hz, 3H, CH$_3$), 1.37 (br s, 2H, NH$_2$), 3.84 (q, J=4.6 Hz, 1H, CH—CH$_3$), 6.93 (dd, J=7.8, 4.8 Hz, 1H, ArH), 7.38 (ddd, J=7.8, 2.1, 1.5 Hz, 1H, ArH), 8.15 (dd, J=4.8, 1.5 Hz, 1H, ArH), 8.27 (d, J=2.1 Hz, 1H, ArH).

Screening

Establishment of TEL:JAK cell lines

The coding region encompassing nucleotides 1–487 of TEL was amplified by PCR using the oligonucleotides 5TEL (5'-GGA GGATCC TGA TCT CTC TCG CTG TGA GAC-3') and 3TEL (5'-AGGC GTCGAC TTC TTC TTC ATG GTT CTG-3') and U937 mRNA as template. A BamHI site was present into the 5TEL Primer, a SalI site was incorporated into the 3TEL primer. The regions encompassing the kinase domains of JAK2 (nucleotides 2994–3914; JAK2F 5'-ACGC GTC GAC GGT GCC TTT GAA GAC CGG GAT-3'; JAK2R 5'-ATA GTT TAGCGGCCG CTC AGA ATG AAG GTC ATT T-3') and JAK3 (nucleotides 2520–3469; JAK3F 5'-GAA GTCGAC TAT GCC TGC CAA GAC CCC ACG ATC TT-3'; JAK3R 5'-GGA TCTAGA CTA TGA AAA GGA CAG GGA GTG GTG TTT-3') were generated by PCR using Taq DNA Polymerase (Gibco/BRL) and U937 mRNA as template. A SalI site was incorporated into the forward primer of JAK2 and JAK3, a NotI site was incorporated into the JAK2 reverse primer and a Xba I site was added to the reverse primer of JAK3.

A TEL/Jak2 fusion was generated by digestion of the TELPCR product with BamHI/SalI, digestion of the JAK2 PCR product with SalI/NotI followed by ligation and subcloning into the mammalian expression Vector pTRE 2 (Clontech) digested with BamHI-NotI (pTELJAK2). For JAK3 SalI/NotI cleaved kinase domain PCR product was ligated with BamHI/SalI cleaved TELproduct followed by ligation into BamHI/NotI cleaved pTRE2 (pTELJAK3).

The growth factor dependent myelomonocytic cell line BaF3 bearing the pTET-off plasmid (Clontech) was transfected with either pTELJAK2 or pTELJAK3 and the cells selected for factor independent growth. BaF 3 wild type cells were cultured in DMEM 10% FCS, 10% WEHI 3B conditioned medium. BaF3 TELJAK cells were cultured in DMEM 10% Tet-System Approved FBS (without WEHI 3B conditioned medium).

Cellular Assays were Performed as Follows:

Cell suspensions were prepared by harvesting cells from culture. (Cells used in this test should be in later log phase growth and high viability.) Cells were diluted in correct growth medium to 1.1×final concentration (from 50000 cell/mL to 200,000 cell/mL, depending on cell line).

Compounds to be tested were added (10 μL, 10×final concentration) to a flat bottom 96-well plate. The cellular suspension (90 μL per well) was added, and the plate incubated for 40 hr at 37° C., 5% CO$_2$. MTT (20 μL per well, 5 mg/mL in PBS) was added and the plates were returned to the incubator for a further 6 hours. Lysis buffer (100 μL per well, 10% SDS, 0.01N HCl) was added and the plate stored in the incubator overnight. The plate was then read at 590 nm.

Kinase assays were performed either in a 96 well capture based ELISA assay or in 384 well Optiplates (Packard) using an Alphascreen Protein Tyrosine Kinase kit. In either casse using approximately 1.5 mg of affinity purified PTK domain in the presence of 50 mM HEPES, pH 7.5, 10 mM MgCl2, 150 mM NaCl and 10 mM-1 mM ATP. The biotinylated substrate biotin?EGPWLEEEEEAYGWMDF?NH2 (final concentration 5 mM) was used as substrate. In the ELISA assay tyrosine phosphorylation was quantitated following transfer to an avidin coated ELISA plate using peroxidase linked anti-phospho-tyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSO, with DMSO concentrations never exceeding 1%."

RESULTS

The activity of a range of compounds is shown in Table 1. Compounds that exhibited a capacity to inhibit 50% of cell growth at a concentration of 50 μM (measured under standard conditions, see Methods), are designated as "+".

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

FIGURES AND TABLES

Table 1: 2-amino-6-carba-disubstituted pyrazine and 2-amino-6-carba-disubstituted pyridine possessing growth inhibitory activity (>50%) in transformed cell lines (Tel-Jak2 and Tel-Jak3) at 50 μM

| Chemistry | Jak2 | Jak3 | DU145 |
|---|---|---|---|
| Chemistry 44 | + | + | + |
| Chemistry 51 | + | + | NT |
| Chemistry 68 | + | + | NT |
| Chemistry 69 | + | + | NT |

-continued
| Chemistry | Jak2 | Jak3 | DU145 |
|---|---|---|---|
| 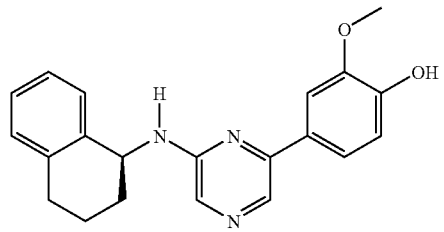<br>Chemistry 87 | + | − | NT |
| 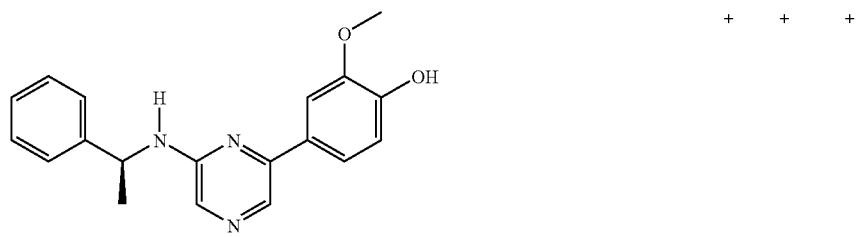<br>Chemistry 118 | + | + | + |
| 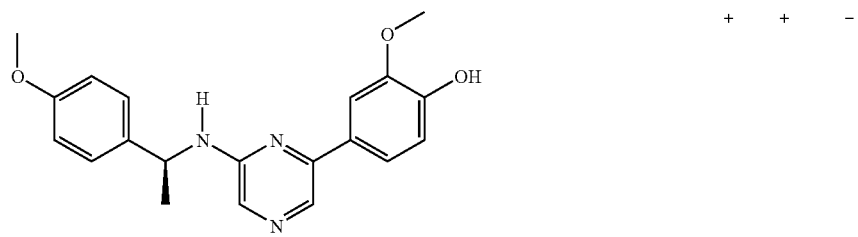<br>Chemistry 117 | + | + | − |
| 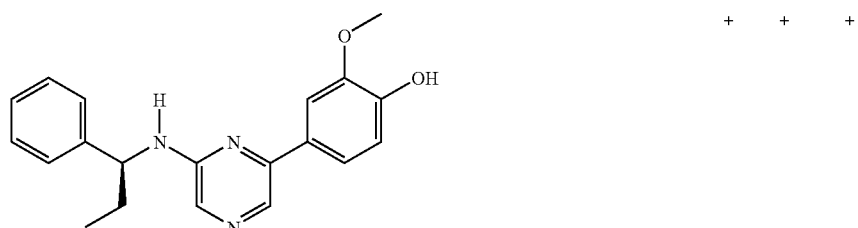<br>Chemistry 119 | + | + | + |
| 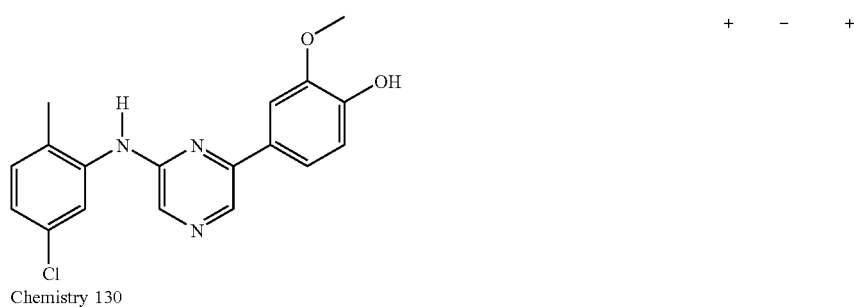<br>Chemistry 130 | + | − | + |

-continued
| Chemistry | Jak2 | Jak3 | DU145 |
|---|---|---|---|
| 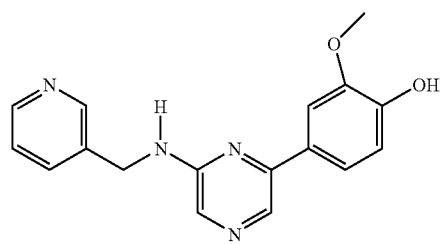
Chemistry 136 | + | + | + |
| 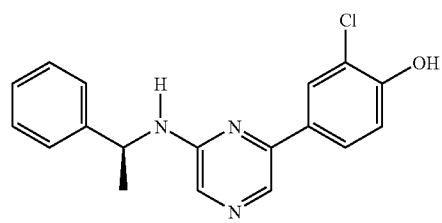
Chemistry 175 | − | + | − |
| 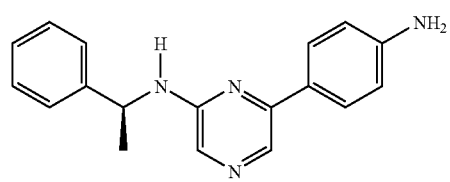
Chemistry 181 | + | + | − |
| 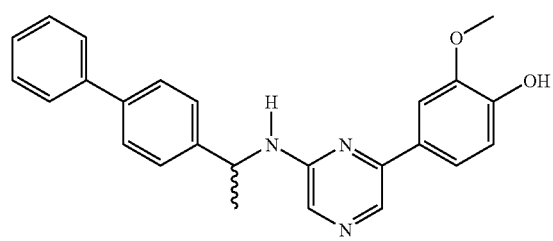
Chemistry 185 | + | + | − |
| 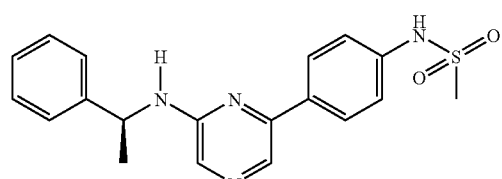
Chemistry 192 | + | + | + |
| 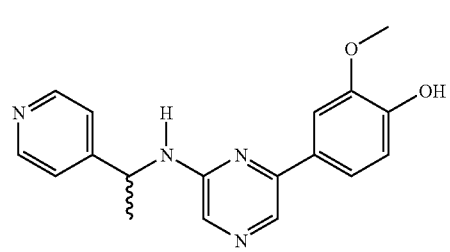
Chemistry 200 | + | + | − |

-continued
| Chemistry | Jak2 | Jak3 | DU145 |
|---|---|---|---|
| 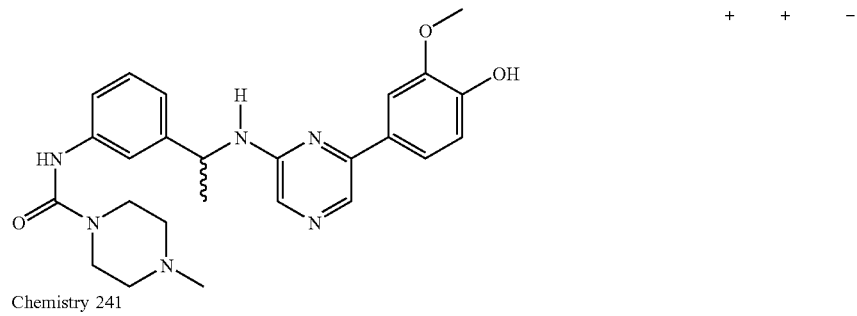  Chemistry 241 | + | + | − |
| 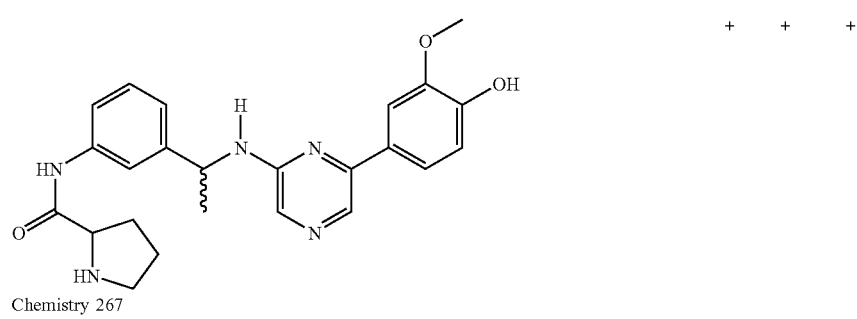  Chemistry 267 | + | + | + |
| 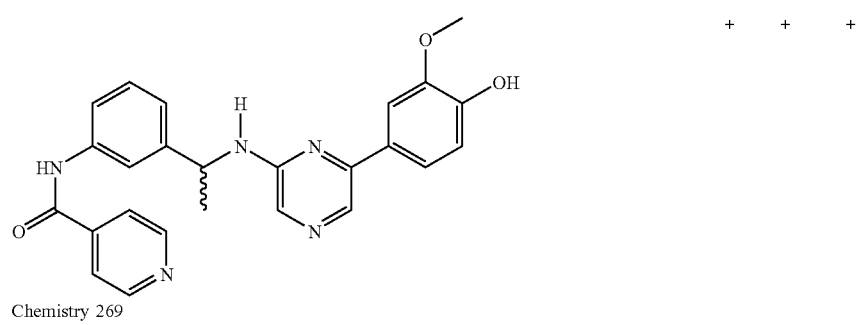  Chemistry 269 | + | + | + |
| 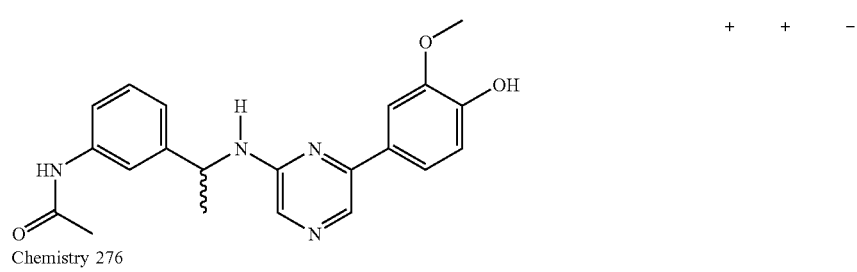  Chemistry 276 | + | + | − |
| 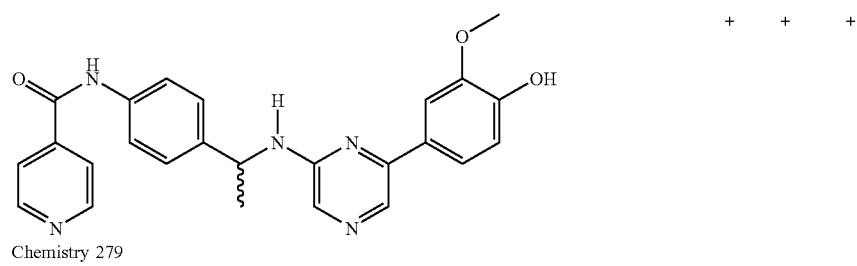  Chemistry 279 | + | + | + |

-continued
| Chemistry | Jak2 | Jak3 | DU145 |
|---|---|---|---|
| 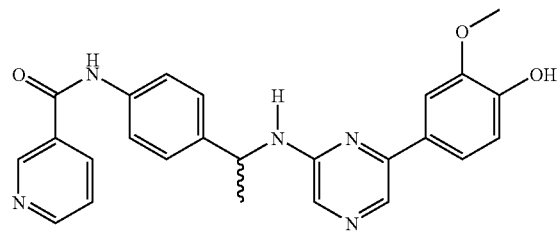
Chemistry 280 | + | + | − |
| 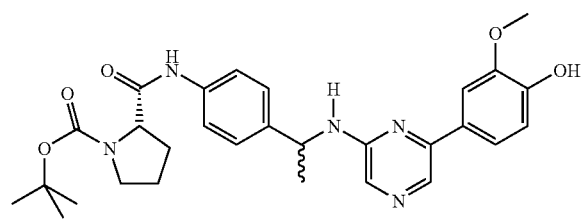
Chemistry 281 | + | + | + |
| 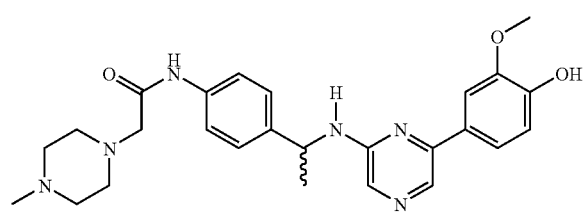
Chemistry 282 | + | + | + |
| 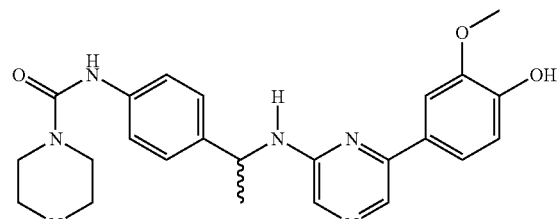
Chemistry 283 | + | + | + |
| 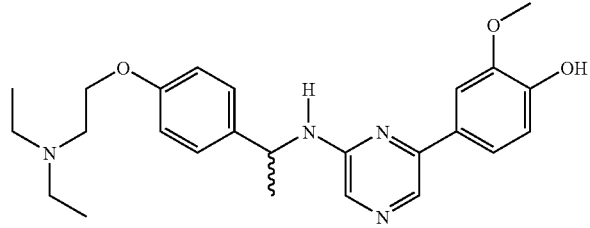
Chemistry 285 | + | + | + |
| 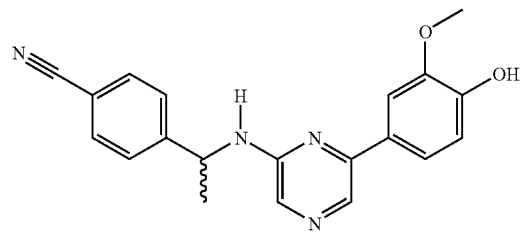
Chemistry 303 | + | + | − |

-continued
| Chemistry | Jak2 | Jak3 | DU145 |
|---|---|---|---|
| 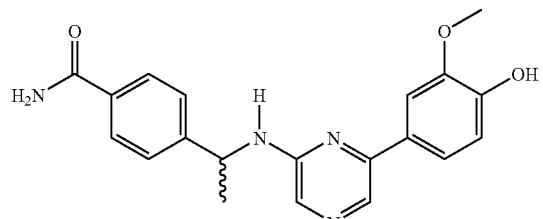<br>Chemistry 304 | + | + | − |
| 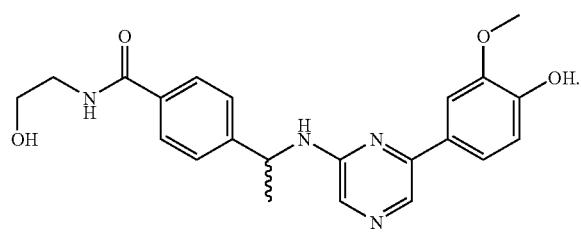<br>Chemistry 374 | + | + | − |
| 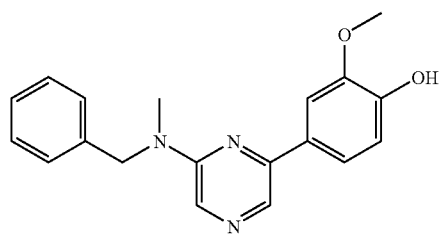<br>Chemistry 137 | + | + | − |
| 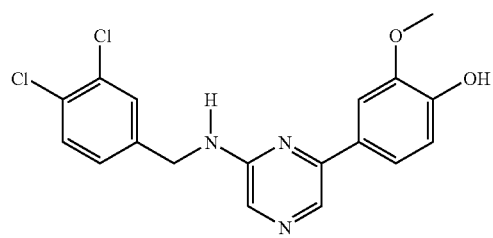<br>Chemistry 139 | + | + | − |
| 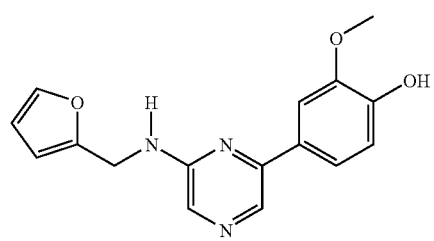<br>Chemistry 141 | + | + | + |

-continued
| Chemistry | Jak2 | Jak3 | DU145 |
|---|---|---|---|
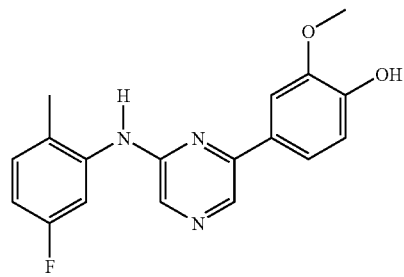
Chemistry 144
+ + −
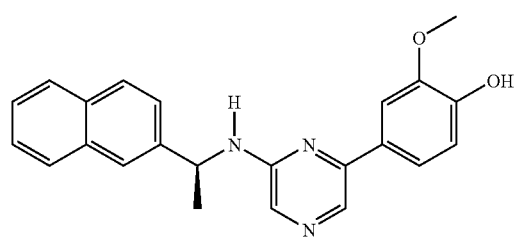
Chemistry 155
+ + −
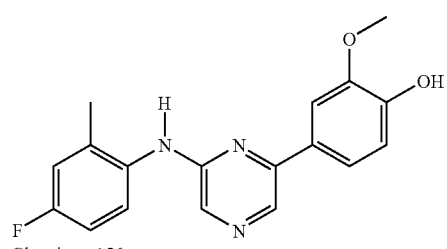
Chemistry 156
+ + −
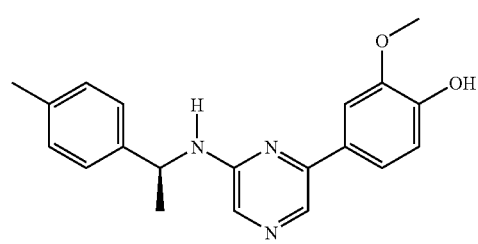
Chemistry 157
+ + −
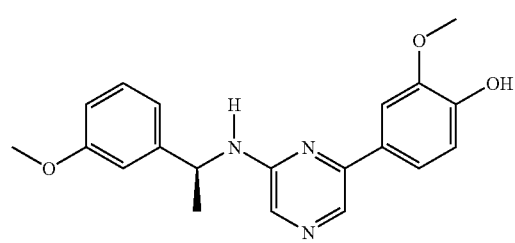
Chemistry 158
+ + +

-continued
| Chemistry | Jak2 | Jak3 | DU145 |
|---|---|---|---|
| 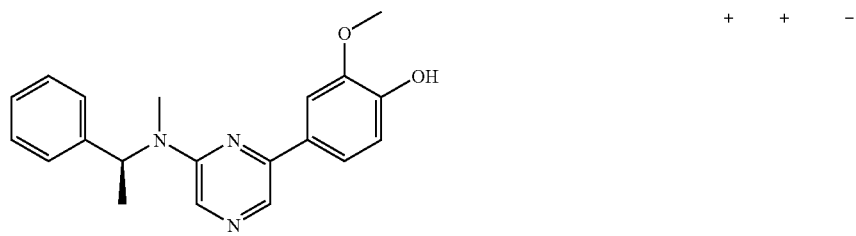  Chemistry 142 | + | + | − |
| 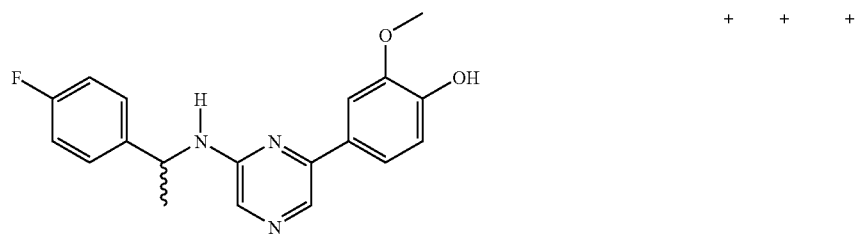  Chemistry 157 | + | + | + |
| 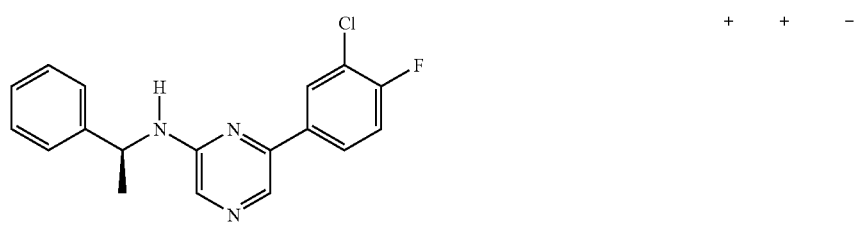  Chemistry 174 | + | + | − |
| 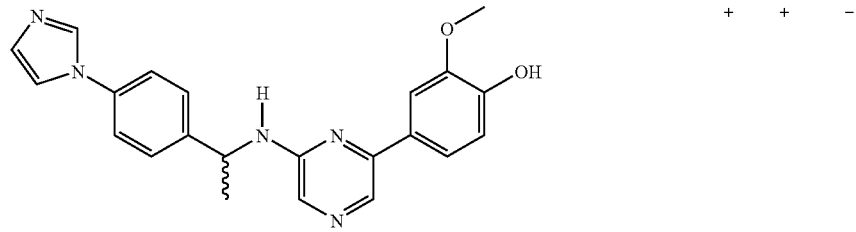  Chemistry 186 | + | + | − |
| 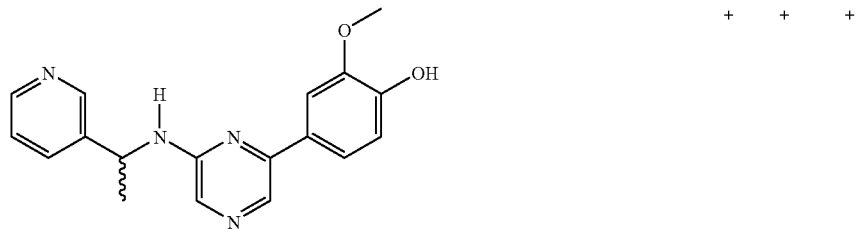  Chemistry 187 | + | + | + |
| 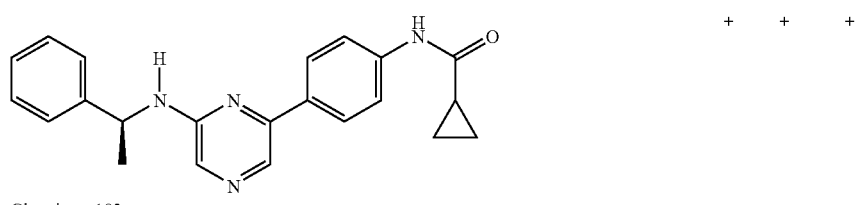  Chemistry 193 | + | + | + |

| Chemistry | Jak2 | Jak3 | DU145 |
|---|---|---|---|
| 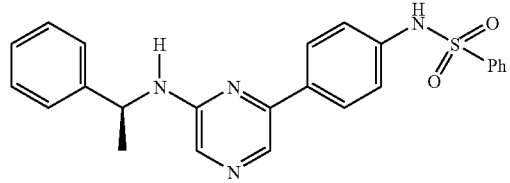<br>Chemistry 226 | + | + | + |
| 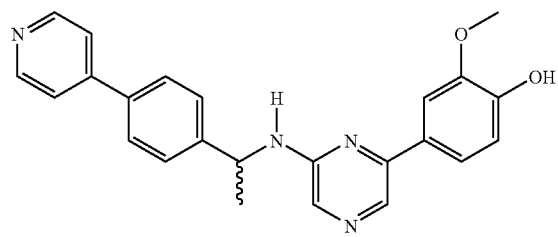<br>Chemistry 266 | + | + | + |
| 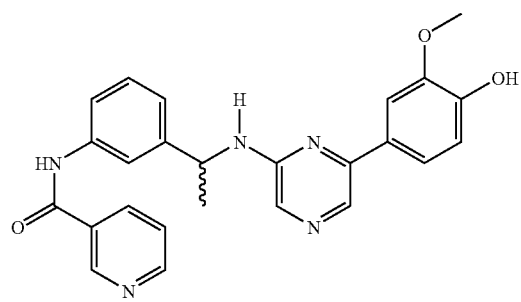<br>Chemistry 268 | + | + | + |
| 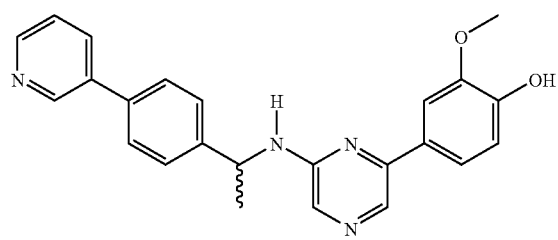<br>Chemistry 270 | + | + | + |
| 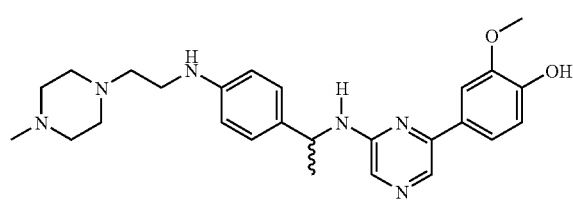<br>Chemistry 318 | + | + | − |
| 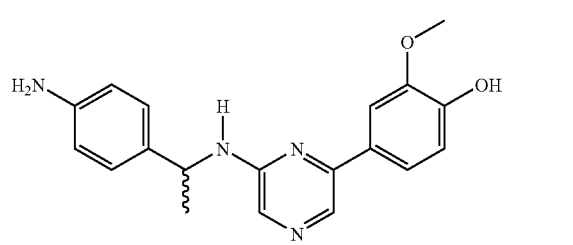<br>Chemistry 319 | + | + | − |

-continued
| Chemistry | Jak2 | Jak3 | DU145 |
|---|---|---|---|
| 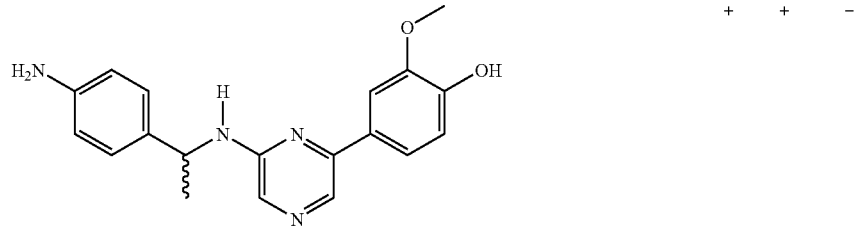<br>Chemistry 319 | + | + | − |
| 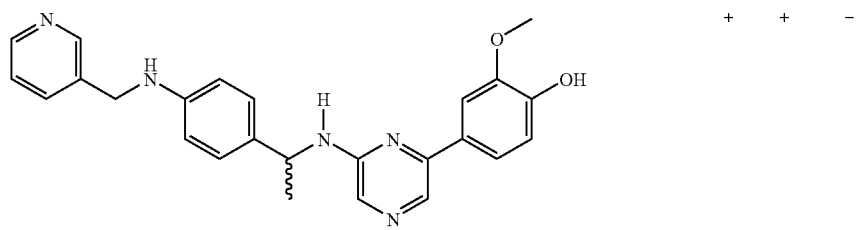<br>Chemistry 320 | + | + | − |
| 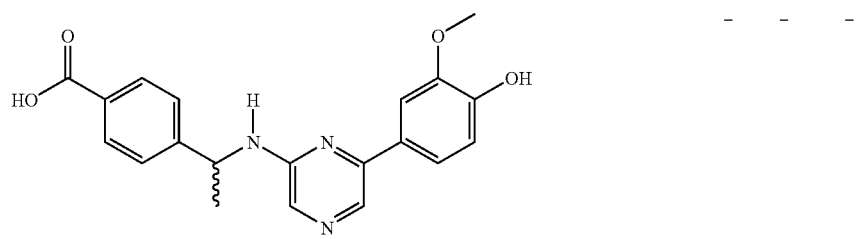<br>Chemistry 324 | − | − | − |
| 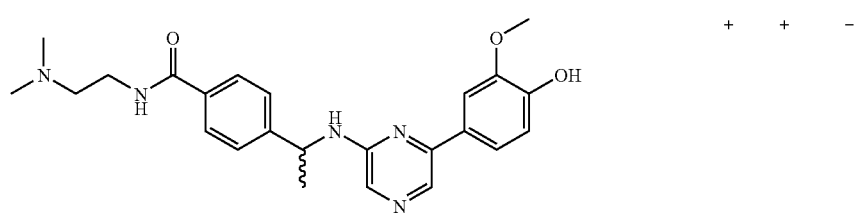<br>Chemistry 352 | + | + | − |
| 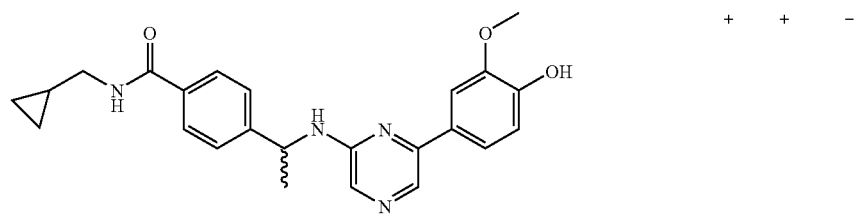<br>Chemistry 354 | + | + | − |
| 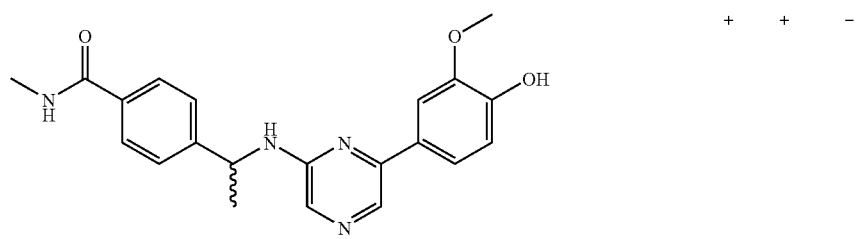<br>Chemistry 370 | + | + | − |

| Chemistry | Jak2 | Jak3 | DU145 |
|---|---|---|---|
| 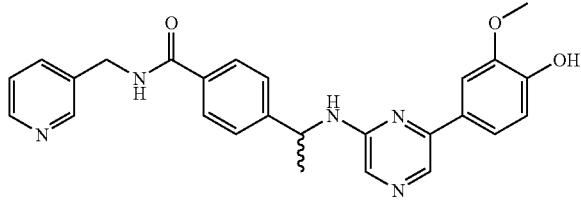<br>Chemistry 372 | + | + | − |

REFERENCES

Spiotto M T, and Chung T D. (2000) STAT3 mediates IL-6-induced growth inhibition in the human prostate cancer cell line LNCaP. *Prostate* 42 88–98

The invention claimed is:

1. A compound of the general formula

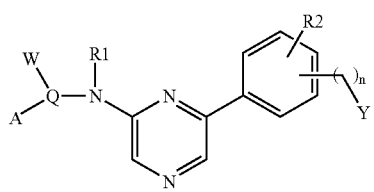

or pharmaceutically acceptable salts, hydrates, or diastereomers thereof, wherein:

$R^1$ is H, $C_{1-4}$ alkyl;

Q is a bond, or $C_{1-4}$ alkyl;

A is aryl, hetaryl optionally substituted with 0–3 substituents independently chosen from halogen, $C_{1-4}$ alkyl, $CH_2F$, $CHF_2$, $CF_3$, CN, aryl, hetaryl, $OCF_3$, $OC_{1-4}$ alkyl, $OC_{2-5}$alkyl$NR^4R^5$, O-aryl, O-heteroaryl, $CO_2R^4$, $CONR^4R^5$, nitro, $NR^4R^5$, $C_{1-4}$ alkyl$NR^4R^5$, $NR^6$ $C_{1-4}$alkyl$NR^4R^5$, $NR^4COR^5$, $NR^6CONR^{45}$, $NR^4SO_2R^5$; and $R^4$ and $R^5$ are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3–8 membered ring optionally containing an atom selected from O, S, $NR^7$; and $R^6$ is selected from H, $C_{1-4}$ alkyl; and $R^7$ is selected H, $C_{1-4}$ alkyl, aryl, hetaryl, $C_{1-4}$ alkyl aryl, $C_{1-4}$ alkyl hetaryl;

$R^2$ is 0–2 substituents independently selected from halogen, $C_{1-4}$alkyl, OH, $OC_{1-4}$alkyl, $CH_2F$, $CHF_2$, $CF_3$, $OCF_3$, CN, $C_{1-4}$alkyl$NR^8R^9$, $OC_{1-4}$alkyl$NR^8R^9$, $CO_2R^8$, $CONR^8R^9$, $NR^8R^9$, $NR^8COR^9$, $NR^{10}CONR^8R^9$, $NR^8SO_2R^9$; and $R^8$, $R^9$ are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3–8 membered ring optionally containing an atom selected from O, S, $NR^{11}$; and $R^{10}$ is selected from H, $C_{1-4}$ alkyl, aryl or hetaryl; and $R^{11}$ is selected from H, $C_{1-4}$ alkyl, aryl, hetaryl, $C_{1-4}$ alkyl aryl, $C_{1-4}$ alkyl hetaryl;

Y is halogen, OH, $NR^{12}R^{13}$, $NR^{12}COR^{13}$, $NR^{12}CONR^{13}$, $NR^{12}SO_2R^{13}$; and $R^{12}$, and $R^{13}$ are each independently H, $CH_2F$, $CHF_2$, $CF_3$, CN, $C_{1-4}$ alkyl, $C_{1-4}$ alkyl cycloalkyl, $C_{1-4}$ alkyl cyclohetalkyl, or may be joined to form an optionally substituted 3–6 membered ring optionally containing an atom selected from O, S, $NR^{14}$ and $R^{14}$ is selected from H, $C_{1-4}$ alkyl;

n=0–4;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, $OC_{1-4}$ alkyl, $NR^{15}R^{16}$; and $R^{15}$ and $R^{16}$ are each independently H, $C_{1-4}$ alkyl, $C_{1-4}$ alkyl cycloalkyl, $C_{1-4}$ alkyl cyclohetalkyl, or may be joined to form an optionally substituted 3–8 membered ring optionally containing an atom selected from O, S, $NR^{17}$; and $R^{17}$ is selected from H, $C_{1-4}$ alkyl;

when Y is OH or $NHCOCH_3$ then $R^2$ is 1–2 substituents; and when Y is $NH_2$ and $R^2$ is absent then Y is in the para position.

2. A compound according to claim 1 selected from compounds of the general formula II:

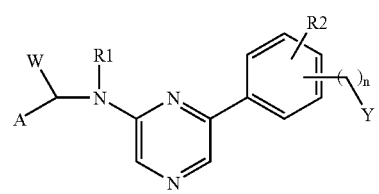

or pharmaceutically acceptable salts, hydrates, solvates, crystal forms or diastereomers thereof, wherein:

R1 is H, $C_{1-4}$ alkyl;

Q is a bond, or $C_{1-4}$ alkyl;

A is aryl, hetaryl optionally substituted with 0–3 substituents independently chosen from halogen, $C_{1-4}$ alkyl, $CH_2F$, $CHF_2$, $CF_3$, CN, aryl, hetaryl, $OCF_3$, $OC_{1-4}$ alkyl, $OC_{2-5}$alkyl$NR^4R^5$, O-aryl, O-heteroaryl, $CO_2R^4$, $CONR^4R^5$, $NR^4R^5$, $C_{1-4}$alkyl$NR^4R^5$, $NR^6$ $C_{1-4}$alkyl$NR^4R^5$, $NR^4COR^5$, $NR^6CONR^4R^5$, $NR^4SO_2R^5$; and $R^4$ and $R^5$ are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3–8 membered ring optionally containing an atom selected from O, S, $NR^7$; and $R^6$ is selected from H, $C_{1-4}$ alkyl; and $R^7$ is selected from H, $C_{1-4}$ alkyl, aryl, hetaryl, $C_{1-4}$ alkyl aryl, $C_{1-4}$ alkyl hetaryl;

$R^2$ is 0–2 substituents independently selected from halogen, $C_{1-4}$alkyl, OH, $OC_{1-4}$alkyl, $CH_2F$, $CHF_2$, $CF_3$, $OCF_3$, CN, $C_{1-4}$alkyl$NR^8R^9$, $OC_{1-4}$alkyl$NR^8R^9$, $CO_2R^8$, $CONR^8R^9$, $NR^8R^9$, $NR^8COR^9$, NR[10]CONR[8]R[9], NR[8]SO$_2$R[9]; and R[8], R[9] are each independently H, $C_{1-4}$ alkyl, $C_{1-4}$ alkyl cycloalkyl, $C_{1-4}$ alkyl cyclohetalkyl, aryl, hetaryl, $C_{1-4}$ alkyl aryl, $C_{1-4}$ alkyl hetaryl, or may be joined to form an optionally substituted 3–8 membered ring optionally containing an atom selected from O, S, NR[11]; and R[10] is selected from H, $C_{1-4}$ alkyl, aryl or hetaryl; and R[11] is selected from H, $C_{1-4}$ alkyl, aryl, hetaryl, $C_{1-4}$ alkyl aryl, $C_{1-4}$ alkyl hetaryl;

Y is halogen, OH, NR[12]R[13], NR[12]COR[13], NR[12]CONR[13], NR[12]SO$_2$R[13]; and R[12], and R[13] are each independently H, CH$_2$F, CHF$_2$, CF$_3$, CN, $C_{1-4}$ alkyl, $C_{1-4}$ alkyl cycloalkyl, $C_{1-4}$ alkyl cyclohetalkyl, or may b joined to form an optionally substituted 3–6 membered ring optionally containing an atom selected from O, S, NR[14] and R[14] is selected from H, $C_{1-4}$ alkyl;

n=0–4;

W is selected from H, $C_{1-4}$alkyl, $C_{2-6}$alkenyl; where $C_{1-4}$alkyl or $C_{2-6}$alkenyl may be optionally substituted with $C_{1-4}$alkyl, OH, O$C_{1-4}$alkyl, NR[15]R[16]; and R[15] and R[16] are each independently H, $C_{1-4}$ alkyl, $C_{1-4}$ alkyl cycloalkyl, $C_{1-4}$ alkyl cyclohetalkyl, or may be joined to form an optionally substituted 3–8 membered ring optionally containing an atom selected from O, S, NR[17]; and R[17] is selected from H, $C_{1-4}$ alkyl;

when Y is OH or NHCOCH$_3$ then R$^2$ is 1–2 substituents; and when Y is NH$_2$ and R$^2$ is absent then Y is in the para position.

3. A compound according to claim 1 where W is $C_{1-4}$ alkyl wherein the compound possesses S chirality at the chiral carbon bearing W.

4. A compound according to claim 3 wherein the compound is a mixture of R and S isomers and the mixture comprises at least 70% of the S isomer.

5. A compound according to claim 4 wherein the compound comprises at least 80% of the S isomer.

6. A compound according to claim 4 wherein the compound comprises at least 90% of the S isomer.

7. A compound according to claim 4 wherein the compound comprises at least 95% of the S isomer.

8. A compound according to claim 4 wherein the compound comprises at least 99% of the S isomer.

9. A compound according to claim 1 wherein the compound is selected from the group consisting of:

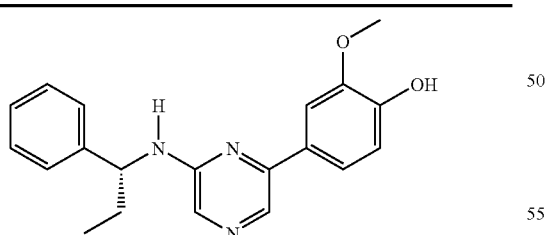

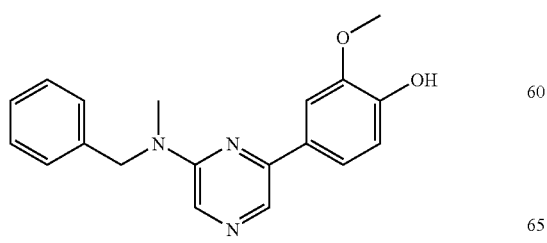

-continued

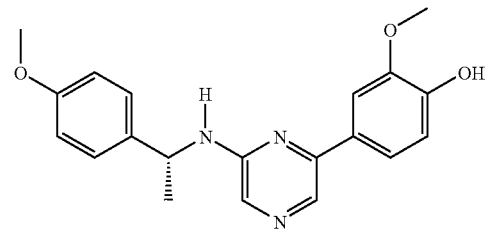

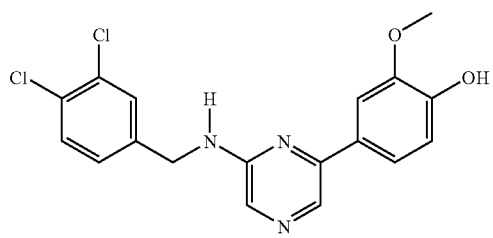

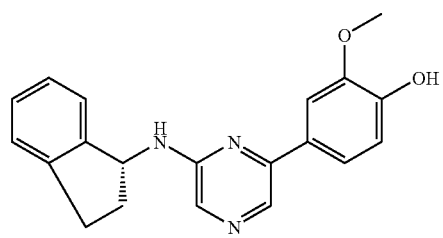

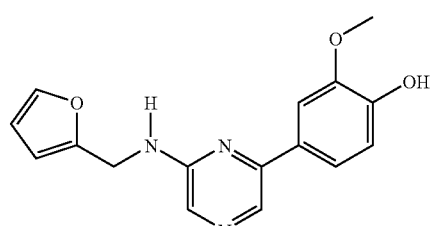

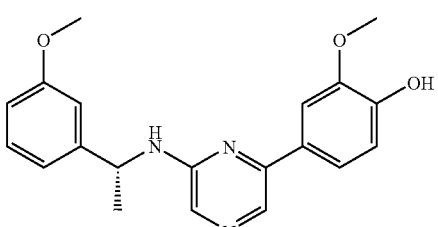

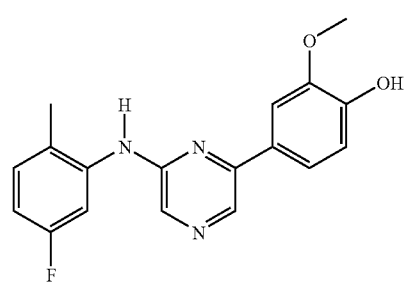

-continued
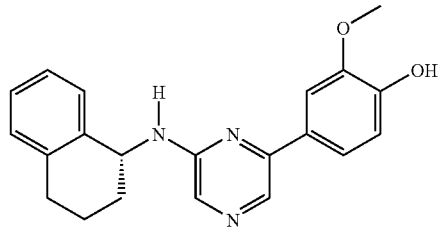
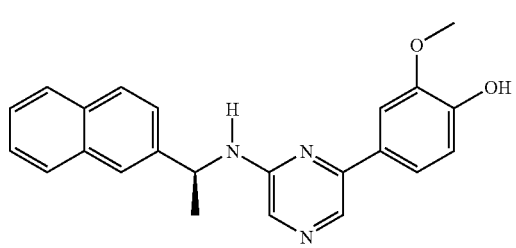
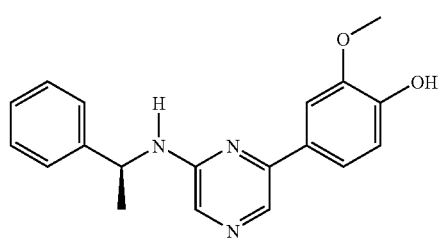
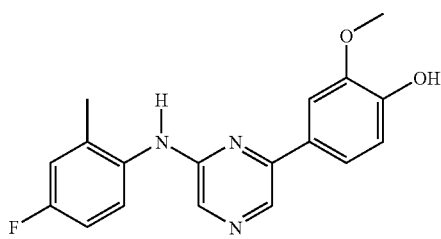
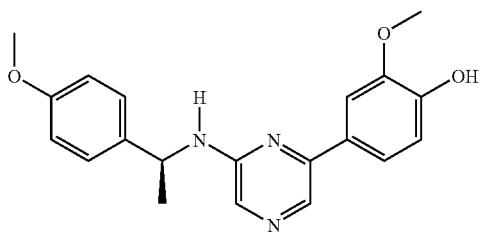
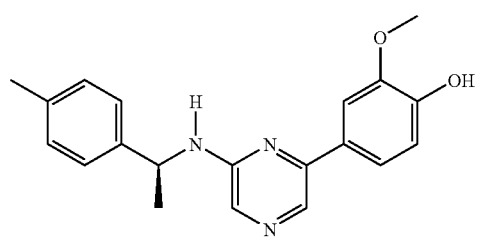
-continued
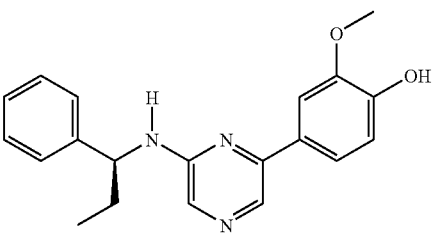
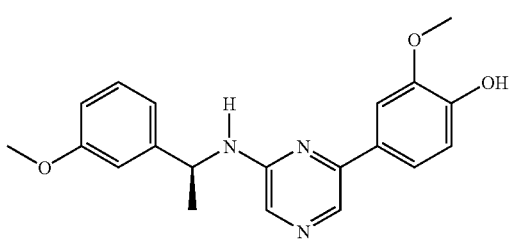
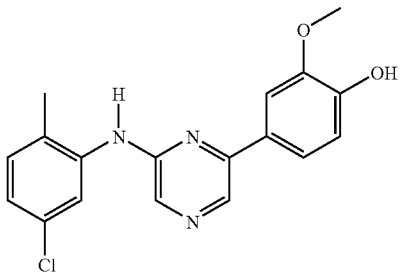
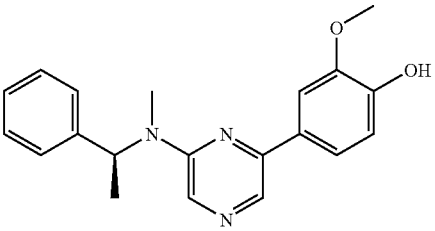
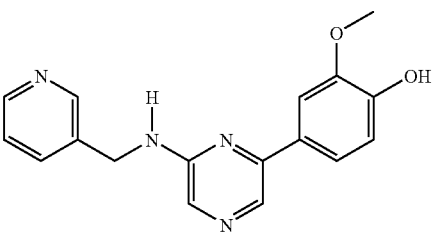
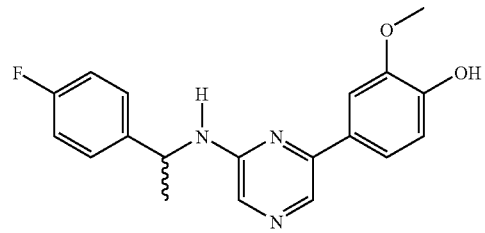

-continued
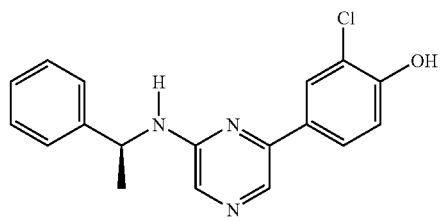
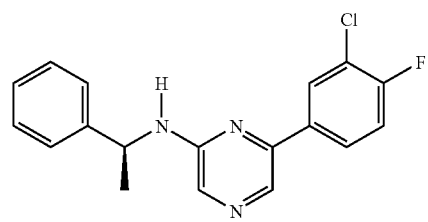
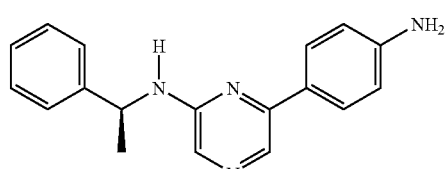
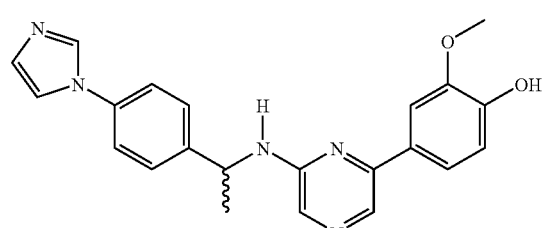
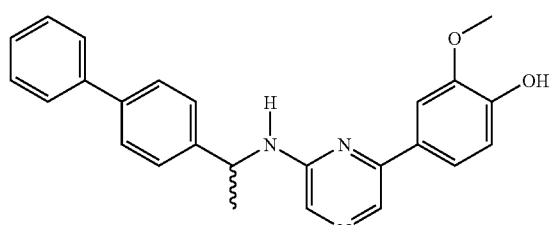
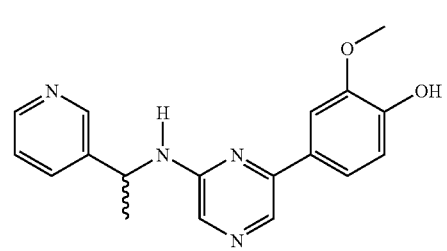
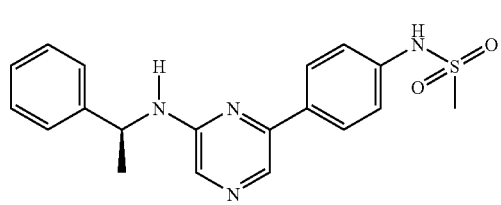
-continued
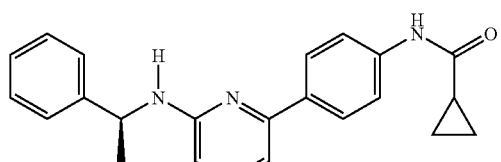
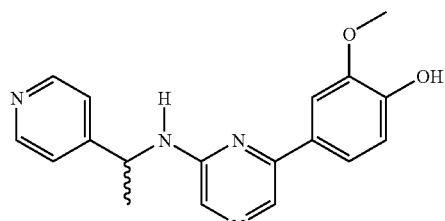
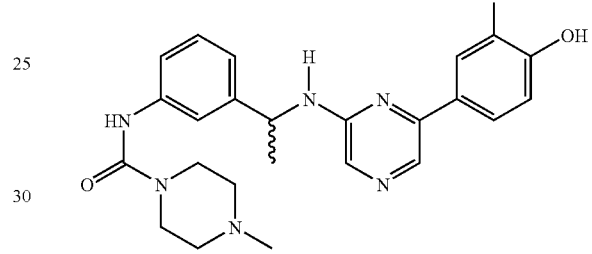
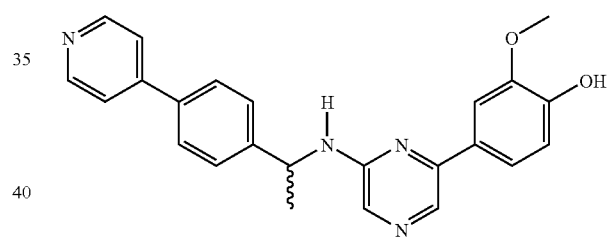
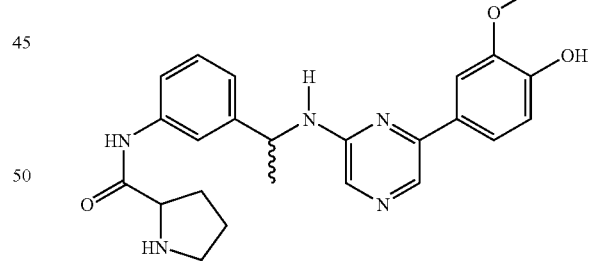
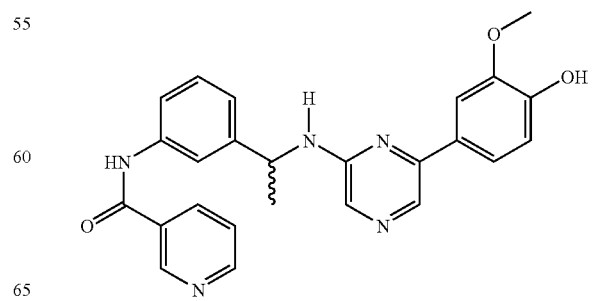

-continued
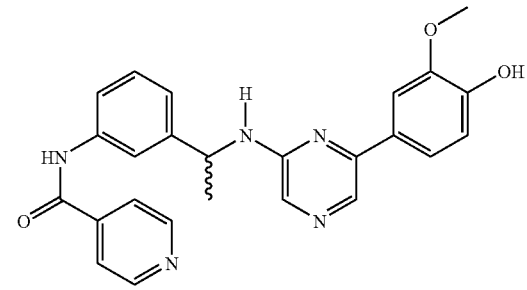
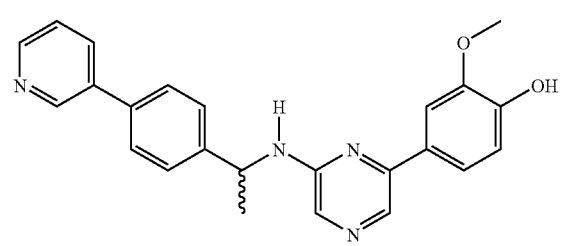
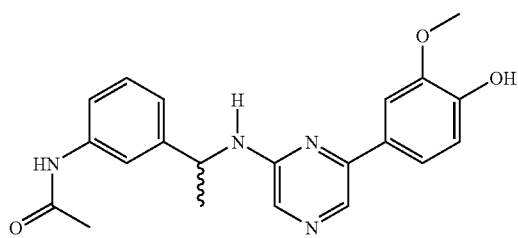
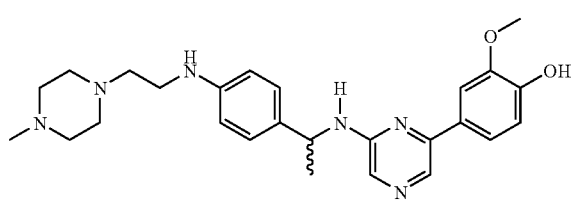
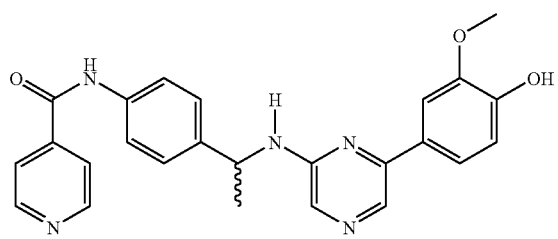
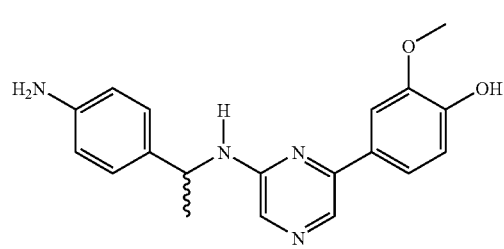
-continued
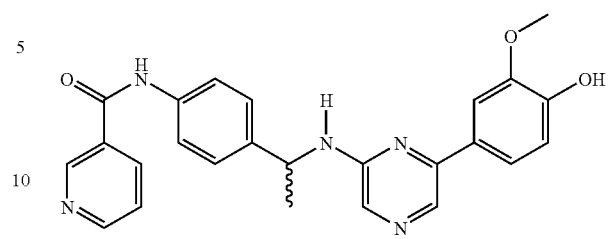
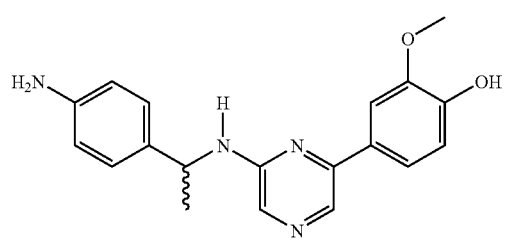
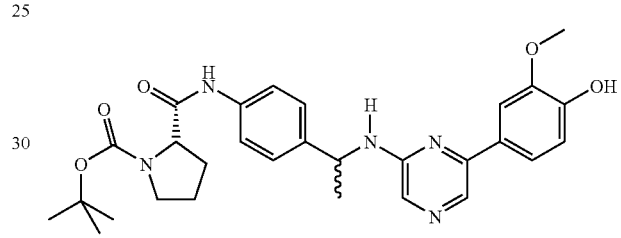
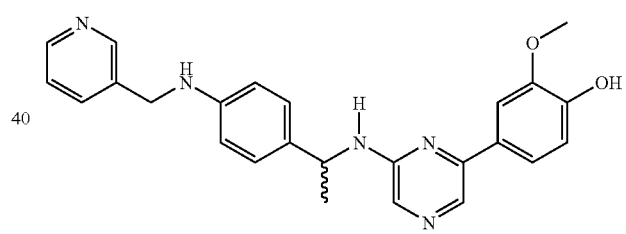
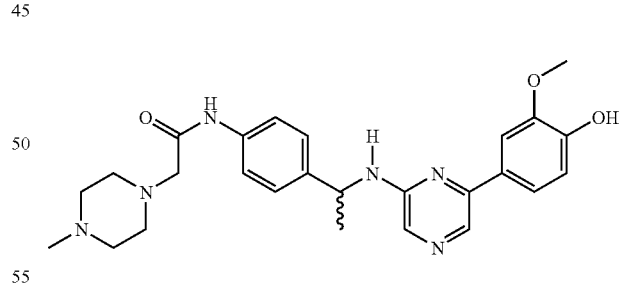
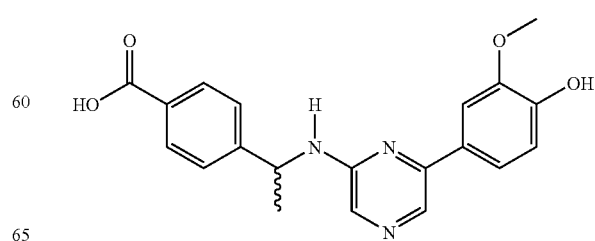

-continued
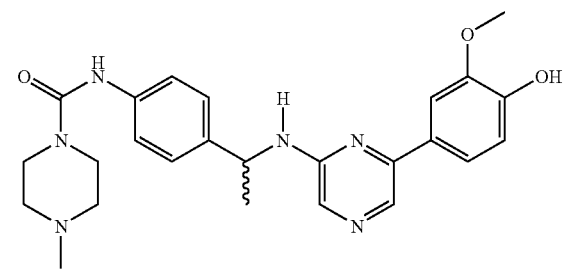
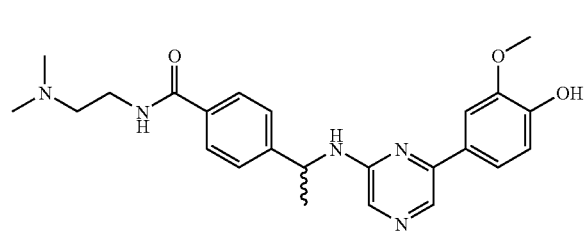
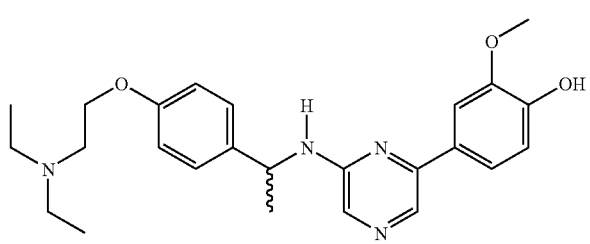
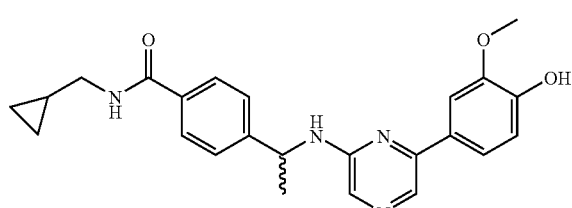
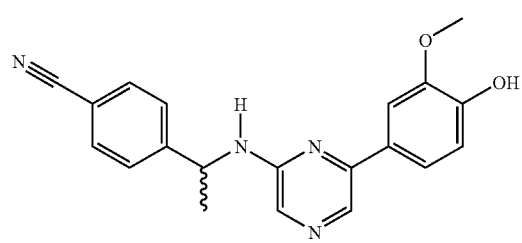
-continued
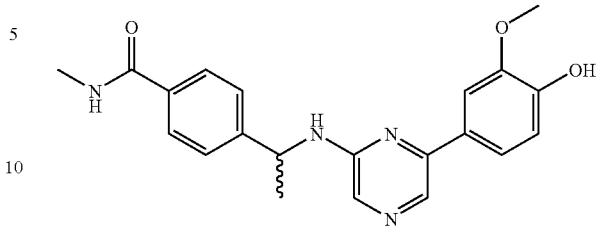
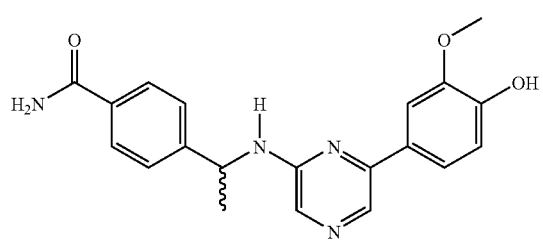
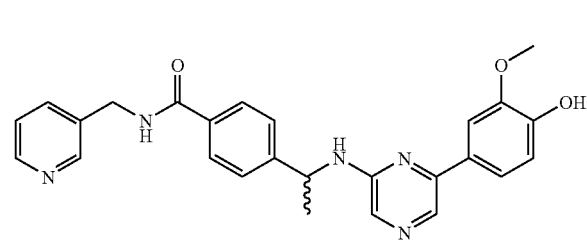
and
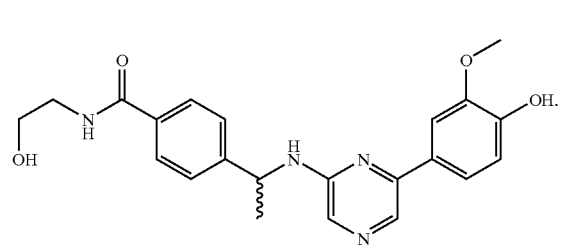
10. A composition comprising a carrier and at least one compound according to claim 1.
11. A pharmaceutical composition comprising at least one of the compounds according to claim 1 and a pharmaceutically acceptable vehicle or diluent.
* * * * *